United States Patent
Asbury et al.

(10) Patent No.: US 9,394,567 B2
(45) Date of Patent: *Jul. 19, 2016

(54) DETECTION AND QUANTIFICATION OF SAMPLE CONTAMINATION IN IMMUNE REPERTOIRE ANALYSIS

(71) Applicant: Sequenta, Inc., South San Francisco, CA (US)

(72) Inventors: Thomas Asbury, San Francisco, CA (US); Victoria Carlton, San Francisco, CA (US); Malek Faham, Pacifica, CA (US); Stephen C. Macevicz, Cupertino, CA (US); Martin Moorhead, San Mateo, CA (US); Thomas Willis, San Francisco, CA (US); Jianbiao Zheng, Fremont, CA (US)

(73) Assignee: ADAPTIVE BIOTECHNOLOGIES CORPORATION, Seattle, WA (US)

( * ) Notice: Subject to any disclaimer, the term of this patent is extended or adjusted under 35 U.S.C. 154(b) by 399 days.

This patent is subject to a terminal disclaimer.

(21) Appl. No.: 13/859,210

(22) Filed: Apr. 9, 2013

(65) Prior Publication Data

US 2013/0302801 A1    Nov. 14, 2013

Related U.S. Application Data

(63) Continuation-in-part of application No. 13/835,093, filed on Mar. 15, 2013, which is a continuation-in-part of application No. 13/100,365, filed on May 4, 2011, which is a continuation-in-part of application No. 12/615,263, filed on Nov. 9, 2009, now Pat. No. 8,236,503, said application No. 13/835,093 is a continuation-in-part of application No. 12/615,263, application No. 13/859,210, which is a continuation-in-part of application No. 13/834,794, filed on Mar. 15, 2013, which is a continuation-in-part of application No. 13/100,365, which is a continuation-in-part of application No. 12/615,263, said application No. 13/834,794 is a continuation-in-part of application No. 12/615,263.

(60) Provisional application No. 61/776,647, filed on Mar. 11, 2013, provisional application No. 61/738,277, filed on Dec. 17, 2012, provisional application No. 61/658,317, filed on Jun. 11, 2012, provisional application No. 61/446,822, filed on Feb. 25, 2011, provisional application No. 61/445,743, filed on Feb. 23, 2011, provisional application No. 61/332,175, filed on May 6, 2010, provisional application No. 61/112,693, filed on Nov. 7, 2008, provisional application No. 61/768,269, filed on Feb. 22, 2013, provisional application No. 61/624,002, filed on Apr. 12, 2012.

(51) Int. Cl.
*C12Q 1/68* (2006.01)
*C12P 19/34* (2006.01)

(52) U.S. Cl.
CPC ............ *C12Q 1/6883* (2013.01); *C12Q 1/6869* (2013.01); *C12Q 2600/158* (2013.01)

(58) Field of Classification Search
USPC ................................................ 435/6.12, 91.2
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,800,159 A | 1/1989 | Mullis et al. |
| 4,942,124 A | 7/1990 | Church |
| 4,965,188 A | 10/1990 | Mullis et al. |
| 5,075,217 A | 12/1991 | Weber |
| 5,149,625 A | 9/1992 | Church et al. |
| 5,168,038 A | 12/1992 | Tecott et al. |
| 5,210,015 A | 5/1993 | Gelfand et al. |
| 5,296,351 A | 3/1994 | Morley et al. |
| 5,364,759 A | 11/1994 | Caskey et al. |
| 5,399,491 A | 3/1995 | Kacian et al. |
| 5,418,134 A | 5/1995 | Morley et al. |
| 5,635,400 A | 6/1997 | Brenner |
| 5,776,737 A | 7/1998 | Dunn |
| 5,837,447 A | 11/1998 | Gorski |

(Continued)

FOREIGN PATENT DOCUMENTS

| EP | 0303459 A2 | 2/1989 |
|---|---|---|
| EP | 0799897 A1 | 10/1997 |

(Continued)

OTHER PUBLICATIONS

PCT/US2013/065493, Appln filed Oct. 17, 2013, Faham et al.

(Continued)

*Primary Examiner* — Kenneth R. Horlick
*Assistant Examiner* — Joyce Tung
(74) *Attorney, Agent, or Firm* — Cooley LLP

(57) ABSTRACT

The invention is directed to methods for detecting and quantifying nucleic acid contamination in a tissue sample of an individual containing T cells and/or B cells, which is used for generating a sequence-based clonotype profile. In one aspect, the invention is implemented by measuring the presence and/or level of an endogenous or exogenous nucleic acid tag by which nucleic acid from an intended individual can be distinguished from that of unintended individuals. Endogenous tags include genetic identity markers, such as short tandem repeats, rare clonotypes or the like, and exogenous tags include sequence tags employed to determine clonotype sequences from sequence reads.

8 Claims, 11 Drawing Sheets

(56) References Cited

U.S. PATENT DOCUMENTS

| | | |
|---|---|---|
| 5,846,719 A | 12/1998 | Brenner et al. |
| 5,854,033 A | 12/1998 | Lizardi |
| 5,925,517 A | 7/1999 | Tyagi et al. |
| 5,935,793 A | 8/1999 | Wong |
| 5,981,176 A | 11/1999 | Wallace |
| 5,981,179 A | 11/1999 | Lorinez et al. |
| 6,087,096 A | 7/2000 | Dau |
| 6,090,592 A | 7/2000 | Adams et al. |
| 6,174,670 B1 | 1/2001 | Wittwer et al. |
| 6,258,568 B1 | 7/2001 | Nyren |
| 6,300,070 B1 | 10/2001 | Boles et al. |
| 6,416,948 B1 | 7/2002 | Pilarski et al. |
| 6,458,530 B1 | 10/2002 | Morris et al. |
| 6,569,627 B2 | 5/2003 | Wittwer et al. |
| 6,787,308 B2 | 9/2004 | Balasubramanian et al. |
| 7,115,400 B1 | 10/2006 | Adessi et al. |
| 7,157,228 B2 | 1/2007 | Hashmi et al. |
| 7,313,308 B2 | 12/2007 | Turner et al. |
| 7,323,305 B2 | 1/2008 | Leamon et al. |
| 7,365,179 B2 | 4/2008 | Brenner |
| 7,393,665 B2 | 7/2008 | Brenner |
| 7,537,897 B2 | 5/2009 | Brenner et al. |
| 7,544,473 B2 | 6/2009 | Brenner |
| 7,833,716 B2 | 11/2010 | Becker et al. |
| 7,862,999 B2 | 1/2011 | Zheng et al. |
| 7,907,800 B2 | 3/2011 | Foquet et al. |
| 7,960,116 B2 | 6/2011 | Eid et al. |
| 8,021,842 B2 | 9/2011 | Brenner |
| 8,053,188 B2 | 11/2011 | Gullberg et al. |
| 8,137,569 B2 | 3/2012 | Harnack et al. |
| 8,137,936 B2 | 3/2012 | Macevicz |
| 8,153,375 B2 | 4/2012 | Travers et al. |
| 8,158,359 B2 | 4/2012 | Leamon et al. |
| 8,236,503 B2 | 8/2012 | Faham et al. |
| 8,313,625 B2 | 11/2012 | Rothberg et al. |
| 8,318,433 B2 | 11/2012 | Brenner |
| 8,445,205 B2 | 5/2013 | Brenner |
| 8,481,292 B2 | 7/2013 | Casbon et al. |
| 8,507,205 B2 | 8/2013 | Faham et al. |
| 8,628,927 B2 | 1/2014 | Faham et al. |
| 2002/0076725 A1 | 6/2002 | Toyosaki-Maeda et al. |
| 2005/0250147 A1 | 11/2005 | Macevicz |
| 2005/0260570 A1 | 11/2005 | Mao et al. |
| 2006/0019304 A1 | 1/2006 | Hardenbol et al. |
| 2006/0234234 A1 | 10/2006 | Van Dongen et al. |
| 2006/0263789 A1 | 11/2006 | Kincaid |
| 2007/0020640 A1 | 1/2007 | McCloskey et al. |
| 2007/0117134 A1 | 5/2007 | Kou |
| 2007/0172873 A1 | 7/2007 | Brenner et al. |
| 2007/0264653 A1 | 11/2007 | Berlin et al. |
| 2009/0098555 A1 | 4/2009 | Roth et al. |
| 2009/0105959 A1 | 4/2009 | Braverman et al. |
| 2009/0226975 A1 | 9/2009 | Sabot et al. |
| 2010/0137143 A1 | 6/2010 | Rothberg et al. |
| 2010/0151471 A1 | 6/2010 | Faham et al. |
| 2010/0300895 A1 | 12/2010 | Nobile et al. |
| 2010/0304982 A1 | 12/2010 | Hinz et al. |
| 2010/0323348 A1 | 12/2010 | Hamady et al. |
| 2011/0160078 A1 | 6/2011 | Fodor et al. |
| 2011/0195253 A1 | 8/2011 | Hinz et al. |
| 2011/0207134 A1 | 8/2011 | Faham et al. |
| 2011/0207135 A1 | 8/2011 | Faham et al. |
| 2011/0207617 A1 | 8/2011 | Faham et al. |
| 2012/0035062 A1 | 2/2012 | Schultz et al. |
| 2012/0071331 A1 | 3/2012 | Casbon et al. |
| 2012/0073667 A1 | 3/2012 | Schultz et al. |
| 2012/0135409 A1 | 5/2012 | Faham et al. |
| 2012/0143531 A1 | 6/2012 | Davey et al. |
| 2012/0172241 A1 | 7/2012 | Rearick et al. |
| 2012/0173158 A1 | 7/2012 | Hubbell |
| 2013/0005584 A1 | 1/2013 | Faham et al. |
| 2013/0017957 A1 | 1/2013 | Faham et al. |
| 2013/0065768 A1 | 3/2013 | Zheng et al. |
| 2013/0136799 A1 | 5/2013 | Faham et al. |
| 2013/0150252 A1 | 6/2013 | Faham et al. |
| 2013/0196328 A1 | 8/2013 | Pepin et al. |
| 2013/0202718 A1 | 8/2013 | Pepin et al. |
| 2013/0236895 A1* | 9/2013 | Faham et al. ............... 435/6.11 |
| 2013/0267427 A1 | 10/2013 | Faham et al. |
| 2013/0324422 A1 | 12/2013 | Faham et al. |
| 2013/0344066 A1 | 12/2013 | Faham et al. |
| 2014/0255929 A1* | 9/2014 | Zheng ........................ 435/6.11 |

FOREIGN PATENT DOCUMENTS

| | | |
|---|---|---|
| EP | 0972081 B1 | 6/2007 |
| EP | 1544308 B1 | 1/2009 |
| JP | 4262799 A | 9/1992 |
| JP | 2007-536939 A | 12/2007 |
| WO | WO 03/052101 A1 | 6/2003 |
| WO | WO 2005/111242 A2 | 11/2005 |
| WO | WO 2010/053587 A2 | 5/2010 |
| WO | WO 2011/106738 A2 | 9/2011 |
| WO | WO 2011/139371 A1 | 11/2011 |
| WO | WO 2011/139372 A1 | 11/2011 |
| WO | WO 2011/140433 A2 | 11/2011 |
| WO | WO 2012/061832 A1 | 5/2012 |
| WO | WO 2012/083225 A2 | 6/2012 |
| WO | WO 2012/142213 A2 | 10/2012 |
| WO | WO 2013/036459 A2 | 3/2013 |
| WO | WO 2013/055595 A1 | 4/2013 |
| WO | WO 2013/066726 A1 | 5/2013 |
| WO | WO 2013/085855 A1 | 6/2013 |
| WO | WO 2013/086462 A1 | 6/2013 |
| WO | WO 2013/090390 A2 | 6/2013 |
| WO | WO 2013/090469 A1 | 6/2013 |
| WO | WO 2013/096480 A2 | 6/2013 |
| WO | WO 2013/134162 A2 | 9/2013 |
| WO | WO 2013/134302 A1 | 9/2013 |
| WO | WO 2013/155119 A1 | 10/2013 |
| WO | WO 2013/158936 A1 | 10/2013 |
| WO | WO 2013/181428 A2 | 12/2013 |
| WO | WO 2013/188471 A2 | 12/2013 |
| WO | WO 2014/018460 A1 | 1/2014 |
| WO | WO 2014/026031 A1 | 2/2014 |

OTHER PUBLICATIONS

PCT/US2013/065509, Appln filed Oct. 17, 2013, Faham et al.
PCT/US2013/065757, Appln filed Oct. 18, 2013, Faham et al.
PCT/US2014/017416, Appln filed Feb. 20, 2014, Pepin et al.
U.S. Appl. No. 12/615,263, filed Nov. 9, 2011, Faham et al.
U.S. Appl. No. 12/945,678, filed Nov. 12, 2010, Faham et al.
U.S. Appl. No. 13/100,365, filed May 4, 2011, Faham et al.
U.S. Appl. No. 13/100,389, filed May 4, 2011, Faham et al.
U.S. Appl. No. 13/100,395, filed May 4, 2011, Faham et al.
U.S. Appl. No. 13/174,086, filed Jun. 30, 2011, Faham et al.
U.S. Appl. No. 13/196,885, filed Aug. 2, 2011, Moorhead et al.
U.S. Appl. No. 13/214,111, filed Aug. 19, 2011, Faham et al.
U.S. Appl. No. 13/369,031, filed Feb. 8, 2012, Faham et al.
U.S. Appl. No. 13/459,701, filed Apr. 30, 2012, Faham et al.
U.S. Appl. No. 13/468,323, filed May 10, 2012, Faham et al.
U.S. Appl. No. 13/487,980, filed Jun. 4, 2012, Faham et al.
U.S. Appl. No. 13/596,581, filed Aug. 28, 2012, Zheng et al.
U.S. Appl. No. 13/627,497, filed Sep. 26, 2012, Faham et al.
U.S. Appl. No. 13/688,414, filed Nov. 29, 2012, Faham et al.
U.S. Appl. No. 13/834,794, filed Mar. 15, 2013, Pepin et al.
U.S. Appl. No. 13/835,093, filed Mar. 15, 2013, Faham et al.
U.S. Appl. No. 13/861,941, filed Apr. 12, 2013, Pepin et al.
U.S. Appl. No. 13/908,813, filed Jun. 3, 2013, Faham et al.
U.S. Appl. No. 14/075,075, filed Nov. 8, 2013, Faham et al.
U.S. Appl. No. 14/089,517, filed Nov. 25, 2013, Han.
U.S. Appl. No. 14/173,712, filed Feb. 5, 2014, Faham et al.
U.S. Appl. No. 14/176,551, filed Feb. 10, 2014, Faham et al.
U.S. Appl. No. 14/185,846, filed Feb. 20, 2014, Pepin et al.
U.S. Appl. No. 14/197,615, filed Mar. 5, 2014, Carlton et al.
U.S. Appl. No. 14/202,990, filed Mar. 10, 2014, Zheng.
U.S. Appl. No. 14/242,520, filed Apr. 1, 2014, Klinger et al.
U.S. Appl. No. 14/343,286, filed Mar. 6, 2014, Faham et al.
Altschul, et al. Basic local alignment search tool. J Mol Biol. Oct. 5, 1990;215(3):403-10.

(56) References Cited

OTHER PUBLICATIONS

Aslanzadeh. Preventing PCR amplification carryover contamination in a clinical laboratory. Ann Clin Lab Sci. 2004 Autumn;34(4):389-96.
Becker-Andre, et al. Absolute mRNA quantification using the polymerase chain reaction (PCR). A novel approach by a PCR aided transcript titration assay (PATTY). Nucleic Acids Res. Nov. 25, 1989;17(22):9437-46.
Bernard, et al. Color multiplexing hybridization probes using the apolipoprotein E locus as a model system for genotyping. Anal Biochem. Sep. 10, 1999;273(2):221-8.
Bonarius, et al. Monitoring the T-cell receptor repertoire at single-clone resolution. PLoS One. Dec. 20, 2006;1:e55.
Buccisano, et al. Monitoring of minimal residual disease in acute myeloid leukemia. Curr Opin Oncol. Nov. 2009;21(6):582-8. doi: 10.1097/CCO.0b013e3283311856.
Campbell et al. Subclonal phylogenetic structures in cancer revealed by ultra-deep sequencing. PNAS 105(35):13081-13086 (2008).
Chiu, et al. Non-invasive prenatal assessment of trisomy 21 by multiplexed maternal plasma DNA sequencing: large scale validity study. BMJ. Jan. 11, 2011;342:c7401. doi: 10.1136/bmj.c7401.
Choi, et al. Clonal evolution in B-lineage acute lymphoblastic leukemia by contemporaneous VH-VH gene replacements and VH-DJH gene rearrangements. Blood. Mar. 15, 1996;87(6):2506-12.
Ding, et al. Clonal evolution in relapsed acute myeloid leukaemia revealed by whole-genome sequencing. Nature. Jan. 11, 2012;481(7382):506-10. doi: 10.1038/nature10738.
Diviacco, et al. A novel procedure for quantitative polymerase chain reaction by coamplification of competitive templates. Gene. Dec. 15, 1992;122(2):313-20.
Eason et al, "Characterization of synthetic DNA bar codes in Saccharomyces cerevisiae gene-deletion strains," Proc. Natl. Acad. Sci., 101(30): 11046-11051 (2004).
European search report and opinion dated Jul. 26, 2013 for EP Application No. 11777704.5.
Freeman, et al. Quantitative RT-PCR: Pitfalls and Potential. Biotechniques. Jan. 1999;26(1):112-22, 124-5.
Gauss, et al. Mechanistic constraints on diversity in human V(D)J recombination. Mol Cell Biol. Jan. 1996;16(1):258-69.
Gerlinger, et al. How Darwinian models inform therapeutic failure initiated by clonal heterogeneity in cancer medicine. Br J Cancer. Oct. 12, 2010;103(8):1139-43. doi: 10.1038/sj.bjc.6605912. Epub Sep. 28, 2010.
Greenberg, et al. Profile of immunoglobulin heavy chain variable gene repertoires and highly selective detection of malignant clonotypes in acute lymphoblastic leukemia. J Leukoc Biol. Jun. 1995;57(6):856-64.
Hawkins, et al. Whole genome amplification—applications and advances. Curr Opin Biotechnol. Feb. 2002;13(1):65-7.
International search report and written opinion dated Jan. 29, 2014 for PCT/US2013/045276.
International search report and written opinion dated Sep. 22, 2011 for PCT Application No. US11/000791.
International search report and written opinion dated Oct. 19, 2011 for PCT Application No. US11/000792.
Jaffe, et al. Classification of lymphoid neoplasms: the microscope as a tool for disease discovery. Blood. Dec. 1, 2008;112(12):4384-99. doi: 10.1182/blood-2008-07-077982.
Ku, et al. Exome sequencing: dual role as a discovery and diagnostic tool. Ann Neurol. Jan. 2012;71(1):5-14. doi: 10.1002/ana.22647.
Kumar, et al. PEG-labeled nucleotides and nanopore detection for single molecule DNA sequencing by synthesis. Sci Rep. 2012;2:684. Epub Sep. 21, 2012.
Larimore, et al. Shaping of human germline IgH repertoires revealed by deep sequencing. J Immunol. Sep. 15, 2012;189(6):3221-30. doi: 10.4049/jimmunol.1201303. Epub Aug. 3, 2012.
Lefranc. IMGT, the international ImMunoGeneTics database. Nucleic Acids Res. Jan. 1, 2003;31(1):307-10.
Leone, et al. Molecular beacon probes combined with amplification by NASBA enable homogeneous, real-time detection of RNA. Nucleic Acids Res. May 1, 1998;26(9):2150-5.
Liedtke, et al. A comparison of methods for RNA extraction from lymphocytes for RT-PCR. PCR Methods Appl. Dec. 1994;4(3):185-7.
Murugan, et al. Statistical inference of the generation probability of T-cell receptors from sequence repertoires. Proc Natl Acad Sci U S A. Oct. 2, 2012;109(40):16161-6. doi: 10.1073/pnas.1212755109. Epub Sep. 17, 2012.
Needleman, et al. A general method applicable to the search for similarities in the amino acid sequence of two proteins. J Mol Biol. Mar. 1970;48(3):443-53.
Petrosino, et al. Metagenomic pyrosequencing and microbial identification. Clin Chem. May 2009;55(5):856-66. doi: 10.1373/clinchem.2008.107565. Epub Mar. 5, 2009.
Pourmand, et al. Direct electrical detection of DNA synthesis. Proc Natl Acad Sci U S A. Apr. 25, 2006;103(17):6466-70. Epub Apr. 13, 2006.
Rothberg, et al. An integrated semiconductor device enabling non-optical genome sequencing. Nature. Jul. 20, 2011;475(7356):348-52. doi: 10.1038/nature10242.
Seo, et al. Four-color DNA sequencing by synthesis on a chip using photocleavable fluorescent nucleotides. Proc Natl Acad Sci U S A. Apr. 26, 2005;102(17):5926-31. Epub Apr. 13, 2005.
Sims, et al. Fluorogenic DNA sequencing in PDMS microreactors. Nat Methods. Jun. 12, 2011;8(7):575-80. doi: 10.1038/nmeth.1629.
Thor Straten, et al. T-cell clonotypes in cancer.J Transl Med. Apr. 8, 2004;2(1):11.
Venturi, et al. A mechanism for TCR sharing between T cell subsets and individuals revealed by pyrosequencing. J Immunol. Apr. 1, 2011;186(7):4285-94. doi: 10.4049/jimmunol.1003898. Epub Mar. 7, 2011.
Vlassov, et al. Circulating nucleic acids as a potential source for cancer biomarkers. Curr Mol Med. Mar. 2010;10(2):142-65.
Abbott, et al. Design and use of signature primers to detect carry-over of amplified material. J Virol Methods. Jan. 1994;46(1):51-9.
Arstila, et al. A direct estimate of the human alphabeta T cell receptor diversity. Science. Oct. 29, 1999;286(5441):958-61.
Batzoglou. The many faces of sequence alignment. Brief Bioinform. Mar. 2005;6(1):6-22.
Baum, et al. Direct measurement of T-cell receptor repertoire diversity with AmpliCot. Nat Methods. Nov. 2006;3(11):895-901.
Bene, et al. How and why minimal residual disease studies are necessary in leukemia: a review from WP10 and WP12 of the European LeukaemiaNet. Haematologica. Aug. 2009;94(8):1135-50. Epub Jul. 7, 2009.
Benichou, et al. Rep-Seq: uncovering the immunological repertoire through next-generation sequencing. Immunology. Mar. 2012;135(3):183-91. doi: 10.1111/j.1365-2567.2011.03527.x.
Bentley, et al. Accurate whole human genome sequencing using reversible terminator chemistry. Nature. Nov. 6, 2008;456(7218):53-9. doi: 10.1038/nature07517.
Boyd et al. Measurement and clinical monitoring of human lymphocyte clonality by massively parallel VDJ pyrosequencing. Sci Transl. Med. 1(12):12ra23 (2009).
Boyd, et al. Individual variation in the germline Ig gene repertoire inferred from variable region gene rearrangements. J Immunol. Jun. 15, 2010;184(12):6986-92. Epub May 21, 2010.
Brenner, et al. In vitro cloning of complex mixtures of DNA on microbeads: physical separation of differentially expressed cDNAs. Proc Natl Acad Sci U S A. Feb. 15, 2000;97(4):1665-70.
Brisco, et al. Determining the repertoire of IGH gene rearrangements to develop molecular markers for minimal residual disease in B-lineage acute lymphoblastic leukemia. J Mol Diagn. May 2009;11(3):194-200. Epub Mar. 26, 2009.
Bruggemann, et al. Clinical significance of minimal residual disease quantification in adult patients with standard-risk acute lymphoblastic leukemia. Blood. Feb. 1, 2006;107(3):1116-23. Epub Sep. 29, 2005.

(56) References Cited

OTHER PUBLICATIONS

Buccisano, et al. Prognostic and therapeutic implications of minimal residual disease detection in acute myeloid leukemia. Blood. Jan. 12, 2012;119(2):332-41. doi: 10.1182/blood-2011-08-363291. Epub Oct. 28, 2011.

Campana, et al. Role of minimal residual disease monitoring in adult and pediatric acute lymphoblastic leukemia. Hematol Oncol Clin North Am. Oct. 2009;23(5):1083-98, vii. doi: 10.1016/j.hoc.2009.07.010.

Campana. Minimal residual disease in acute lymphoblastic leukemia. Semin Hematol. Jan. 2009;46(1):100-6.

Casbon et al, "A method for counting PCR template molecules with application to nex-generation sequencing," Nucleic Acids Research 39(12): e81 (2011).

Choi, et al. Relapse in children with acute lymphoblastic leukemia involving selection of a preexisting drug-resistant subclone. Blood. Jul. 15, 2007;110(2):632-9. Epub Mar. 19, 2007.

Craig et al, "Identification of genetic variants using bar-coded multiplex sequencing," Nature Methods, 5(10): 887-893 (2008) and Supplemental Materials.

Dean, et al. Rapid amplification of plasmid and phage DNA using Phi 29 DNA polymerase and multiply-primed rolling circle amplification. Genome Res. Jun. 2001;11(6):1095-9.

Drmanac, et al. Human genome sequencing using unchained base reads on self-assembling DNA nanoarrays. Science. Jan. 1, 2010;327(5961):78-81. doi: 10.1126/science.1181498. Epub Nov. 5, 2009.

Eichler, et al. Haplotype and interspersion analysis of the FMR1 CGG repeat identifies two different mutational pathways for the origin of the fragile X syndrome. Hum Mol Genet. Mar. 1996;5(3):319-30.

Eid, et al. Real-time DNA sequencing from single polymerase molecules. Science. Jan. 2, 2009;323(5910):133-8. doi: 10.1126/science.1162986. Epub Nov. 20, 2008.

Frank, "BARCRAWL and BARTAB: software tools for the design and implementation of barcoded primers for highly multiplexed DNA sequencing," BMC Bioinformatics, 10: 362 (Oct. 29, 2009).

Freeman, et al. Profiling the T-cell receptor beta-chain repertoire by massively parallel sequencing. Genome Res. Oct. 2009;19(10):1817-24. doi: 10.1101/gr.092924.109. Epub Jun. 18, 2009.

Fu et al, "Counting individual DNA molecules by the stochastic attachment of diverse labels," Proc. Natl. Acad. Sci., 108(22): 9026-9031 (2011).

Gloor et al, "Microbiome profiling by Illumina sequencing of combinatorial sequence-tagged PCR products," PLoS ONE 5(10): e15406 (2010).

Hamady, et al. Error-correcting barcoded primers for pyrosequencing hundreds of samples in multiplex. Nat Methods. Mar. 2008;5(3):235-7. doi: 10.1038/nmeth.1184. Epub Feb. 10, 2008.

Han, et al. Immunorepertoire analysis by multiplex PCR amplification and high throughput sequencing . The Journal of Immunology, 2009; 182, 42.6. Abastract only.

He, et al. IgH gene rearrangements as plasma biomarkers in Non-Hodgkin's lymphoma patients. Oncotarget. Mar. 2011;2(3):178-85.

Heger, M. Studies Highlight Challenges of Immune Repertoire Sequencing's Clinical Applicability. Available at http://www.genomeweb.com/sequencing/studies-highlight-challenges-immune-repertoire-sequencings-clinical-applicabilit?hq_e=el&hq_m=966798&hq_l=10&hq_v=2357e2f0b3. Accessed Apr. 6, 2011.

Hensel et al, "Simultaneous identification of bacterial virulence genes by negative selection," Science, 269(5222): 400-403 (1995).

Hosono, et al. Unbiased whole-genome amplification directly from clinical samples. Genome Res. May 2003;13(5):954-64. Epub Apr. 14, 2003.

International search report and written opinion dated Aug. 7, 2013 for PCT/US2013/035857.

Kedzierska, et al. Tracking phenotypically and functionally distinct T cell subsets via T cell repertoire diversity. Mol Immunol. Feb. 2008;45(3):607-18. Epub Aug. 24, 2007.

Kim, et al. Polony multiplex analysis of gene expression (PMAGE) in mouse hypertrophic cardiomyopathy. Science. Jun. 8, 2007;316(5830):1481-4.

Kinde et al, "Detection and quantification of rare mutations with massively parallel sequencing," Proc. Natl. Acad. Sci., 108: 9530-9535 (2011) and Supporting Information.

Kivioja et al, "Counting absolute numbers of molecules using unique molecular identifiers," Nature Methods, 9(1): 72-76 (2012).

Langerak, et al. Polymerase chain reaction-based clonality testing in tissue samples with reactive lymphoproliferations: usefulness and pitfalls. A report of the BIOMED-2 Concerted Action BMH4-CT98-3936. Leukemia. Feb. 2007;21(2):222-9. Epub Dec. 14, 2006.

Li, et al. Utilization of Ig heavy chain variable, diversity, and joining gene segments in children with B-lineage acute lymphoblastic leukemia: implications for the mechanisms of VDJ recombination and for pathogenesis. Blood. Jun. 15, 2004;103(12):4602-9. Epub Mar. 9, 2004.

Logan, et al. High-throughput VDJ sequencing for quantification of minimal residual disease in chronic lymphocytic leukemia and immune reconstitution assessment. Proc Natl Acad Sci U S A. Dec. 27, 2011;108(52):21194-9. Epub Dec. 12, 2011.

Lovisa, et al. IGH and IGK gene rearrangements as PCR targets for pediatric Burkitt's lymphoma and mature B-ALL MRD analysis. Lab Invest. Oct. 2009;89(10):1182-6. Epub Aug. 10, 2009.

Mackay, et al. Real-time PCR in virology. Nucleic Acids Res. Mar. 15, 2002;30(6):1292-305.

Margulies, et al. Genome sequencing in microfabricated high-density picolitre reactors. Nature. Sep. 15, 2005;437(7057):376-80. Epub Jul. 31, 2005.

McCloskey et al, "Encoding PCR products with batch-stamps and barcodes," Biochem. Genet., 45: 761-767 (2007).

Meleshko, et al. Rearrangements of IgH, TCRD and TCRG genes as clonality marker of childhood acute lymphoblastic leukemia. Exp Oncol. Dec. 2005;27(4):319-24.

Meyer et al, "Targeted high-throughput sequencing of tagged nucleic acid samples," Nucleic Acids Research, 35(15): e97 (2007).

Miner et al, "Molecular barcodes detect redundancy and contamination in hairpin-bisulfite PCR," Nucleic Acids Research, 32(17): e135 (2004).

Neale, et al. Comparative analysis of flow cytometry and polymerase chain reaction for the detection of minimal residual disease in childhood acute lymphoblastic leukemia. Leukemia. May 2004;18(5):934-8.

Nguyen et al, "Identification of errors introduced during high throughput sequencing of the T cell receptor repertoire," BMC Genomics, 12: 106 (2011).

Ogle, et al. Direct measurement of lymphocyte receptor diversity. Nucleic Acids Res. Nov. 15, 2003;31(22):e139.

Panzer-Grumayer, et al. Immunogenotype changes prevail in relapses of young children with TEL-AML1-positive acute lymphoblastic leukemia and derive mainly from clonal selection. Clin Cancer Res. Nov. 1, 2005;11(21):7720-7.

Parameswaran et al, "A pyrosequencing-tailored nucleotide barcode design unveils opportunities for large-scale sample multiplexing," Nucleic Acids Research, 35(19): e130 (2007).

Qui et al, "DNA sequence-based "bar codes" for tracking the origins of expressed sequence tags from a maize cDNA library constructed using multiple mRNA sources," Plant Physiology, 133(2): 475-481 (2003).

Reddy, et al. Systems analysis of adaptive immunity by utilization of high-throughput technologies. Curr Opin Biotechnol. Aug. 2011;22(4):584-9. Epub May 12, 2011.

Robins, et al. Ultra-sensitive detection of rare T cell clones. Immunol Methods. Jan. 31, 2012;375(1-2):14-9. Epub Sep. 10, 2011.

Salzberg, "Mind the gaps," Nature Methods, 7(2): 105-106 (2010).

Schmitt et al, "Detection of ultra-rare mutations by next-generation sequencing," Proc. Natl. Acad. Sci., 109(36): 14508-14513 (2012) and Supporting Information.

Shiroguchi et al, "Digital RNA sequencing minimizes sequence-dependent bias and amplification noise with optimized single-molecule barcodes," Proc. Natl. Acad. Sci., 109(4): 1347-1352 (2012).

(56) References Cited

OTHER PUBLICATIONS

Shoemaker et al, "Quantitative phenotypic analysis of yeast deletion mutants using a highly parallel molecular barcoding strategy," Nature Genetics, 14(4): 450-456 (1996).

Smith, et al. Comparison of biosequences. Advances in Applied Mathematics. 1981; 2:482-489.

Sramkova, et al. Detectable minimal residual disease before allogeneic hematopoietic stem cell transplantation predicts extremely poor prognosis in children with acute lymphoblastic leukemia. Pediatr Blood Cancer. Jan. 2007;48(1):93-100.

Swarup, et al. Circulating (cell-free) nucleic acids—a promising, non-invasive tool for early detection of several human diseases. FEBS Lett. Mar. 6, 2007;581(5):795-9. Epub Feb. 2, 2007.

Van Dongen, et al. Design and standardization of PCR primers and protocols for detection of clonal immunoglobulin and T-cell receptor gene recombinations in suspect lymphoproliferations: report of the BIOMED-2 Concerted Action BMH4-CT98-3936. Leukemia. Dec. 2003;17(12):2257-317.

Varley et al, "Nested patch PCR enables highly multiplexed mutation discovery in candidate genes," Genome Research, 18: 1844-1850 (2008).

Wang, et al. Balanced-PCR amplification allows unbiased identification of genomic copy changes in minute cell and tissue samples. Nucleic Acids Res. May 21, 2004;32(9):e76.

Wang, et al. High throughput sequencing reveals a complex pattern of dynamic interrelationships among human T cell subsets. Proc Natl Acad Sci U S A. Jan. 26, 2010; 107(4): 1518-1523.

Wang, et al. Quantitative measurement of pathogen-specific human memory T cell repertoire diversity using a CDR3 beta-specific microarray. BMC Genomics. Sep. 19, 2007;8:329.

Warren, et al. Exhaustive T-cell repertoire sequencing of human peripheral blood samples reveals signatures of antigen selection and a directly measured repertoire size of at least 1 million clonotypes. Genome Res. Feb. 24, 2011. [Epub ahead of print].

Yassai, et al. A clonotype nomenclature for T cell receptors. Immunogenetics. Jul. 2009;61(7):493-502. doi: 10.1007/s00251-009-0383-x. Epub Jul. 1, 2009.

Zaliova, et al. Quantification of fusion transcript reveals a subgroup with distinct biological properties and predicts relapse in BCR/ABL-positive ALL: implications for residual disease monitoring. Leukemia. May 2009;23(5):944-51. Epub Jan. 22, 2009.

Zimmerman, et al. Technical aspects of quantitative competitive PCR. Biotechniques. 1996; 21:268-279.

Chen et al, "Identification of racehorse and sample contamination by novel 24-plex STR system," Forensic Science International: Genetics, 4: 158-167 (2010).

Jabara et al., "Accurate sampling and deep sequencing of the HIV-1 protease gene using a primer ID," Proc. Natl. Acad. Sci., 108(50): 20166-20171 (2011).

Lennon et al, "A scalable, fully automated process for constructon of sequence-ready barcoded libraries for 454." Genome Biology, 11: R15 (2010).

O'Briain et al, "Sorting out mix-ups. The provenance of tissue sections may be confirmed by PCR using microsatellite markers," Am. J. Clin. Pathol., 106(6): 758-764 (1996), (Abstract only).

Qu et al, "Efficient frequency-based de novo short-read clustering for error trimming in next-generation sequencing," Genome Research, 19: 1309-1315 (2009).

Robins et al, "Comprehensive assessmnte of T-cell receptor beta-chain diversity in alpha-beta T cells," Blood, 114(19): 4099-4107 (2009) (including supplemental materials).

Smith et al, "Quantitative pheontyping via deep barcode sequencing," Genome Research, 19: 1836-1842(2009).

Stiller et al, "Direct multiplex sequencing (DMPS)—a novel method for targeted high-throughput sequencing of ancient and highly degraded DNA," Gnome Research, 19: 1843-1848 (2009).

\* cited by examiner

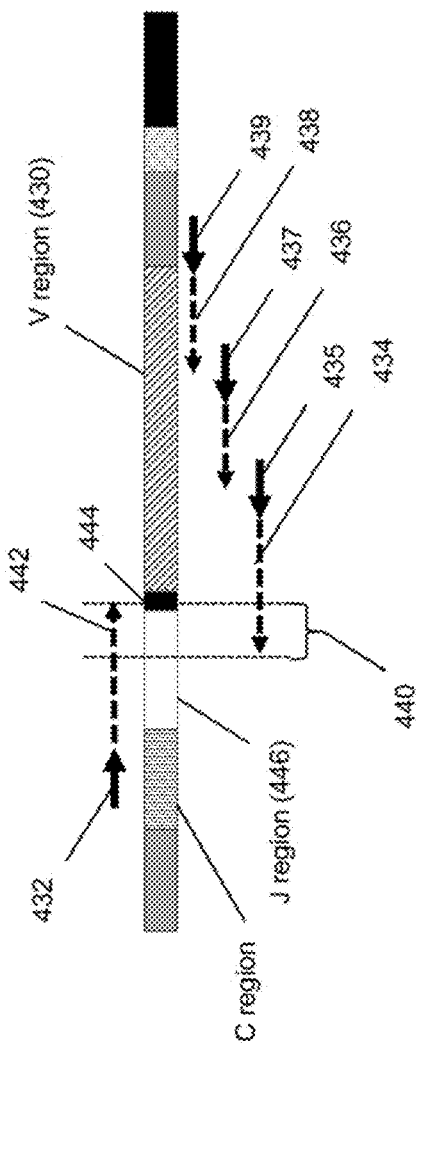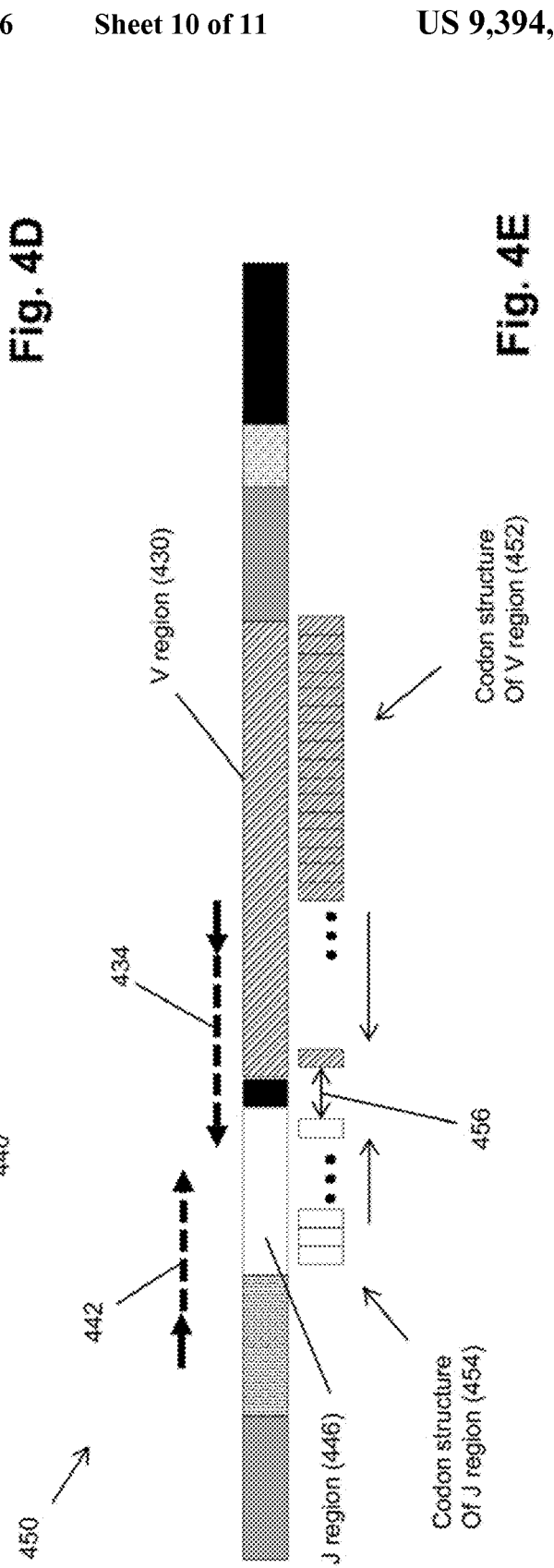

DETECTION AND QUANTIFICATION OF SAMPLE CONTAMINATION IN IMMUNE REPERTOIRE ANALYSIS

This application is a continuation-in-part of U.S. patent application Ser. No. 13/835,093 filed 15 Mar. 2013, which claims priority to U.S. provisional application Ser. No. 61/776,647 filed 11 Mar. 2013; Ser. No. 61/738,277 filed 17 Dec. 2012; and 61/658,317 filed 11 Jun. 2012; Ser. No. 13/835,093 filed 15 Mar. 2013 is a continuation-in-part of Ser. No. 13/100,365 filed 4 May 2011; which claims priority to U.S. provisional application Ser. No. 61/446,822 filed 25 Feb. 2011; Ser. No. 61/445,743 filed 23 Feb. 2011; and Ser. No. 61/332,175 filed 6 May 2010; Ser. No. 13/100,365 is also a continuation-in-part of Ser. No. 12/615,263 filed 9 Nov. 2009 (now U.S. Pat. No. 8,236,503) which claims priority to U.S. provisional application Ser. No. 61/112,693 filed 7 Nov. 2008; and Ser. No. 13/835,093 filed 15 Mar. 2013 is also a continuation-in-part of Ser. No. 12/615,263 filed 9 Nov. 2009 (now U.S. Pat. No. 8,236,503) which claims priority to U.S. provisional application Ser. No. 61/112,693 filed 7 Nov. 2008; all of the foregoing applications being incorporated herein by reference in its entirety.

This application is also a continuation-part of Ser. No. 13/834,794 filed 15 Mar. 2013, which claims priority to U.S. provisional application Ser. No. 61/768,269 filed 22 Feb. 2013; and Ser. No. 13/834,794 is also a continuation-in-part of Ser. No. 13/100,365 filed 4 May. 2011, which claims priority to U.S. provisional application Ser. No. 61/446,822 filed 25 Feb. 2011; Ser. No. 61/445,743 filed 23 Feb. 2011; Ser. No. 61/332,175 filed 6 May. 2010, and Ser. No. 13/100,365 is also a continuation-in-part of Ser. No. 12/615,263 filed 9 Nov. 2009 (now U.S. Pat. No. 8,236,503) which claims priority to U.S. provisional application Ser. No. 61/112,693 filed 7 Nov. 2008; and Ser. No. 13/834,794 filed 15 Mar. 2013 claims priority to U.S. provisional application Ser. No. 61/446,822 filed 25 Feb. 2011; Ser. No. 61/445,743 filed 23 Feb. 2011; Ser. No. 61/332,175 filed 6 May 2010; and Ser. No. 13/834,794 is a continuation-in-part of Ser. No. 12/615,263 filed 9 Nov. 2009 (now U.S. Pat. No. 8,236,503) which claims priority to U.S. provisional application Ser. No. 61/112,693 filed 7 Nov. 2008; all of the foregoing applications being incorporated herein by reference in its entirety.

This application also claims priority from U.S. provisional applications Ser. No. 61/624,002 filed 13 Apr. 2012; Ser. No. 61/658,317 filed 11 Jun. 2012; Ser. No. 61/738,277 filed 17 Dec. 2012; and Ser. No. 61/768,269 filed 22 Feb. 2013; all of the foregoing applications being incorporated herein by reference in its entirety.

BACKGROUND OF THE INVENTION

More and more diagnostic and prognostic applications are being developed that use large-scale DNA sequencing as the per-base cost of DNA sequencing has dropped and sequencing technologies have become more reliable and convenient. e.g. Faham and Willis, U.S. patent publication 2010/0151471; Freeman et al, Genome Research, 19: 1817-1824 (2009); Boyd et al. Sci. Transl. Med., 1(12): 12ra23 (2009): He et al, Oncotarget (Mar. 8, 2011): Palomaki et al, Genet. Med., 14(3): 296-305 (2012); Kohlmann et al., Semin. Oncol., 39(1): 26-36 (2012). In particular, profiles of nucleic acids encoding immune molecules, such as T cell or B cell receptors, or their components, contain a wealth of information on the state of health or disease of an organism, so that the use of such profiles as diagnostic or prognostic indicators has been proposed for a wide variety of conditions, e.g. Faham and Willis (cited above); Boyd et al (cited above); He et al (cited above). Moreover, such sequence-based profiles are capable of much greater sensitivity than approaches based on size distributions of amplified CDR-encoding regions, sequence sampling by microarrays, hybridization kinetics curves from PCR amplicons, or other approaches, e.g. Morley et al. U.S. Pat. No. 5,418,134; van Dongen et al, Leukemia, 17: 2257-2317 (2003); Ogle et al, Nucleic Acids Research, 31: e139 (2003); Wang et al. BMC Genomics, 8: 329 (2007); Baum et al, Nature Methods, 3(11): 895-901 (2006).

However, as in other DNA-based assays that employ amplification steps, the presence of contaminating or cross-contaminating DNA may reduce the effective limit of detection in assays employing immune repertoire sequencing. Sources of contaminating DNA include assay reagents, equipment, operator handling, aersols, and the like, e.g. Urban et al, J. Forensic Sci., 45(6): 1307-1311 (2000); Kwok, pgs. 142-145, in Innis et al, Editors, PCR Protocols (Academic Press, 1990).

Detection of minimal residual disease (MRD) of cancers is impacted by such contamination. Patients treated for many cancers often retain an MRD related to the cancer. That is, even though a patient may have by clinical measures a complete remission of the disease in response to treatment, a small fraction of the cancer cells may remain that have, for one reason or another, escaped destruction. The type and size of this residual population is an important prognostic factor for the patient's continued treatment, e.g. Campana, Hematol. Oncol. Clin. North Am., 23(5): 1083-1098 (2009); Buccisano et al, Blood, 119(2): 332-341 (2012). Thus, the more sensitive the measurement of MRD, the more likely that a subsequent course of treatment will be successful, e.g. Szczepanski et al, Best Pract. Res. Clin. Haematol., 15(1): 37-57 (2002). Several techniques for assessing this population have been developed, including techniques based on flow cytometry, in situ hybridization, cytogenetics, amplification of nucleic acid markers, and the like, e.g. Buccisano et al. Current Opinion in Oncology, 21: 582-588 (2009); van Dongen et al, Leukemia, 17(12): 2257-2317 (2003): and the like. PCR and sequence-based analysis of nucleic acids encoding segments of recombined immune receptors (i.e. clonotypes) have been particularly useful in assessing MRD in leukemias and lymphomas, since such segment (referred to herein as "clonotypes") typically have unique sequences which may serve as molecular tags for their associated cancer cells, e.g. Van Dongen et al (cited above); Faham and Willis, U.S. patent publication 2011/0207134; and the like. Nevertheless, the sensitivity of such techniques is still limited by the presence of cross-over contamination from other individuals.

In view of the potential impact of sequence-based diagnostic and prognostic applications, it would be highly desirable if there were available methods for conveniently detecting and quantifying sample contamination, particularly in assays using immune repertoire sequencing in settings where large numbers of patient samples are processed.

SUMMARY OF THE INVENTION

The present invention is drawn to methods for detecting and quantifying contaminating nucleic acids in immune repertoire assays. The invention is exemplified in a number of implementations and applications, some of which are summarized below and throughout the specification.

In one aspect, the invention is directed to a method for determining a level of contamination in a clonotype profile of a tissue sample comprising T cells and/or B cells of an individual, where the method comprising the steps off (a) obtaining a tissue sample from an individual, the tissue sample comprising nucleic acids from the individual and possibly from one or more other individuals, the nucleic acids including recombined nucleic acids from T cells and/or B cells and non-recombined nucleic acids; (b) generating a clonotype profile from nucleic acid of the tissue sample; (c) sequencing genetic markers at one or more genetic loci of the nucleic acids from the tissue sample to obtain proportions of the nucleic acid from the one or more other individuals and from the individual based on the genetic identification of the individual and the one or more other individuals from the genetic markers, wherein the genetic markers occur at loci present in both the recombined nucleic acids and the non-recombined nucleic acids; and (d) determining the level of contaminating nucleic acid in the clonotype profile as the proportion of the nucleic acid from the one or more other individuals present in the nucleic acid of the tissue sample.

In another aspect, the above method further includes the steps of (i) measuring total amount of said nucleic acids in said tissue sample; (ii) measuring total amount of said recombined nucleic acids in said tissue sample: (iii) sequencing genetic markers at one or more genetic loci in an excisable segment of nucleic acid present in said non-recombined nucleic acids and absent from said recombined nucleic acids to obtain proportions of said non-recombined nucleic acid from said individual and from said one or more other individuals, and (iv) determining said level of contaminating nucleic acid in said clonotype profile from a level of contaminating recombined nucleic acids in said nucleic acid of said tissue sample, the level of contaminating recombined nucleic acids being determined from the total amount of nucleic acids, the total amount of said recombined nucleic acids, said proportions of said nucleic acid from said individual and said one or more other individuals, and the proportions of said non-recombined nucleic acid of said individual and said one or more other individuals.

In a further aspect, the invention is directed to a method for determining a limit of detection of a correlating clonotype in a clonotype profile of a tissue sample comprising T cells and/or B cells of an individual comprising the steps of: (a) obtaining a tissue sample from an individual, the tissue sample comprising nucleic acids from the individual and possibly from one or more other individuals, the nucleic acids including recombined nucleic acids from T cells and/or B cells and non-recombined nucleic acids; (b) generating a clonotype profile from nucleic acid of the tissue sample: (c) sequencing genetic markers at one or more genetic loci of the nucleic acids from the tissue sample to obtain proportions of the nucleic acid from the one or more other individuals and from the individual based on the genetic identification of the individual and the one or more other individuals from the genetic markers, wherein the genetic markers occur at loci present in both the recombined nucleic acids and the non-recombined nucleic acids; and (d) determining the limit of detection as the level of an allele of any of said genetic markers next highest to that of any allele of the one or more loci of the individual.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the invention.

BRIEF DESCRIPTION OF THE DRAWINGS

The novel features of the invention are set forth with particularity in the appended claims. A better understanding of the features and advantages of the present invention is obtained by reference to the following detailed description that sets forth illustrative embodiments, in which the principles of the invention are utilized, and the accompanying drawings of which:

FIG. 4D illustrates the locations of sequence reads generated for an IgH chain. FIG. 4E illustrates the use of the codon structure of V and J regions to improve base calls in the NDN region.

DETAILED DESCRIPTION OF THE INVENTION

The practice of the present invention may employ, unless otherwise indicated, conventional techniques and descriptions of molecular biology (including recombinant techniques), bioinformatics, cell biology, and biochemistry, which are within the skill of the art. Such conventional techniques include, but are not limited to, sampling and analysis of blood cells, nucleic acid sequencing and analysis, and the like. Specific illustrations of suitable techniques can be had by reference to the example herein below. However, other equivalent conventional procedures can, of course, also be used. Such conventional techniques and descriptions can be found in standard laboratory manuals such as *Genome Analysis: A laboratory Manual Series* (Vols. I-IV); *PCR Primer: A Laboratory Manual; and Molecular Cloning: A Laboratory Manual* (all from Cold Spring Harbor Laboratory Press): and the like.

The invention is directed to methods for detecting and quantifying nucleic acid contamination in a tissue sample of an individual that is used for generating a clonotype profile. In particular, the nucleic acid contamination of interest is that originating from other individuals, such as, from patient-to-patient or assay operator-to-patient, carry over contamination, where DNA containing clonotypes from one or more other individuals is inappropriately mixed with DNA of the individual for whom a measurement is intended. The presence of such carry over contamination may lead to spurious estimates of the presence or quantity of clonotypes of great medical interest, such as a clonotype associated with a cancer, such as a leukemia.

Figure 1A:
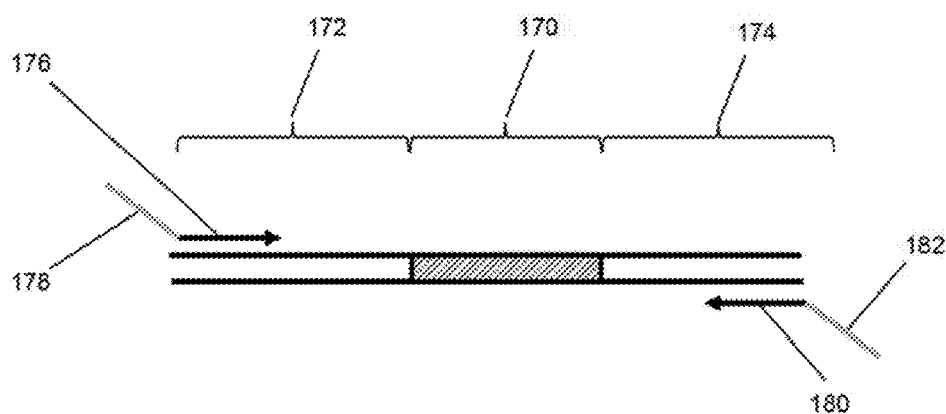
FIG. 1A diagrammatically illustrates a typical scheme for amplifying genetic markers for use in the invention.

In one embodiment, nucleic acid contamination from other individuals may be determined by measuring the amount or proportion of DNA having a genetic identity different from that of the individual of interest, i.e. the individual for whom the measurement or assay is intended. The genetic identity of nucleic acids in a tissue sample may be determined by conventional genetic identification assay that are based on short tandem repeats, single nucleotide polymorphisms, and the like, such as disclosed in the following references, which are incorporated by reference: Caskey et al, U.S. Pat. No. 5,364, 759 Weber U.S. Pat. No. 5,075,217; Shumaker et al, Human Mutation, 7: 346-354 (1996); Sobrino et al, Forensic Sci. Int., 154 (2-3): 181-194 (2005): Mark, Naturvissenchaften, 84: 181-188 (1997); and the like. As illustrated in FIG. 1A, typically, genetic markers in genomic DNA will have a polymorphic region (170) which may contain a SNP or STR along with upstream and downstream flanking regions (172) and (174), respectively, that may be used to locate the genetic marker (170) on the genome and provide primer binding sites for its amplification and analysis. In one embodiment, upstream and downstream primers (176) and (180), respectively, may be used to amplify genetic marker (170) in a two-stage PCR along with recombined nucleic acids from immune cells (as illustrated in FIGS. 2A-2B and 4B-4C). In such embodiment, primers (176) and (180) have tails (178) and (182), respectively, that have sequences that permit the same primers to be used in the amplification of genetic marker (170) as those used to amplify recombined nucleic acids in a second stage of a two-stage PCR. The tails may also contain barcodes or tags that identify the locus of the genetic marker (e.g. to identify it as being from locus 1, 2, 3, or so on, in reference to FIG. 1A). As described below, to the extent possible, the position and lengths of primers (176) and (180) are selected so that their annealing and melting temperatures are approximately the same as those used to amplify the recombined nucleic acids (e.g. (212) of FIG. 2A) and so that the resulting amplicon has approximately the same length and GC content as the amplicons of the recombined nucleic acid molecules.

Figure 1B:
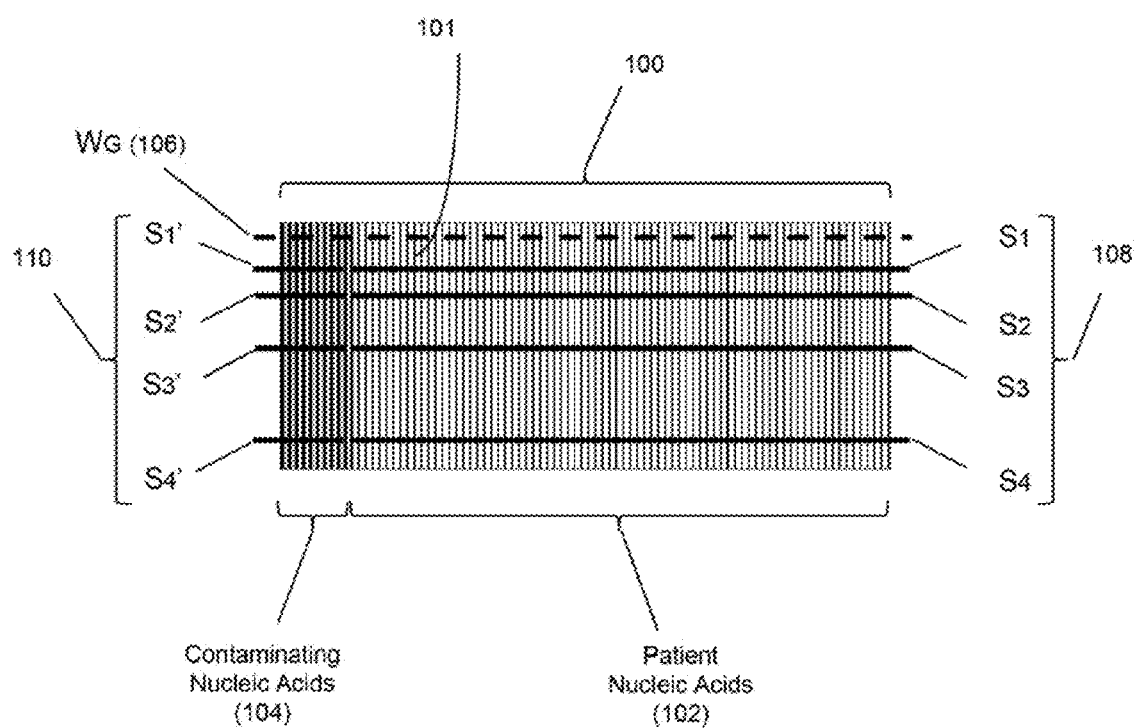
FIG. 1B diagrammatically shows nucleic acid in a sample which comprises patient nucleic acid and contaminating nucleic acid, such as carry over DNA from one or more other patients.
Figure 1C:
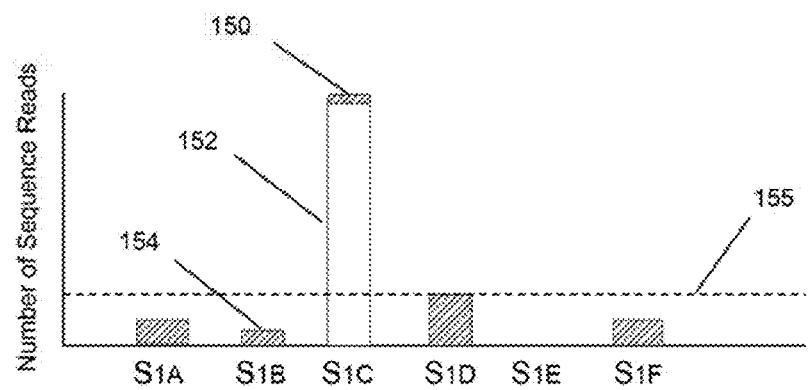
FIG. 1C illustrates the distribution of sequence reads among alleles of a genetic marker at a particular locus.

An exemplary embodiment is illustrated in FIG. 1B. In that figure, nucleic acids (100) extracted from a tissue sample are represented as vertical lines (101) denoting genomes or fragments of genomes both from an individual of interest (102), such as a patient, and from other individuals, that is, contaminating nucleic acids (104). All of the individuals will have genetic markers at sites 1, 2, 3, and 4, which have values $S_1$, $S_2$, $S_1$, and $S_4$ (108) for the individual of interest, and values $S_1'$, $S_2'$, $S_3'$, and $S_1'$ (110) for the contaminating DNA, which of course may include more than one value at each loci if the contamination is from more than one other individual. In any case, as mentioned below, the values for the individual of interest may be distinguished from those of the other individuals that may be present in the tissue sample. If the genetic identity of the individual of interest based on these markers is not known beforehand, it may be determined from information generated in the assay. Assuming that DNA of the individual of interest will be the major fraction of nucleic acids. e.g. 80 percent, 90 percent, 95 percent, or the like, then the distribution of sequence reads corresponding to the different alleles of a genetic marker will be skewed to the allele corresponding to the individual of interest, i.e. the majority allele, as illustrated in FIG. 1C for genetic marker locus 1. For locus 1, let us say that genetic marker. $S_1$, has six alleles, $S_{1A}$, $S_{1B}$, $S_{1C}$, $S_{1D}$, $S_{1E}$ and $S_{1F}$. The allele having the highest number of sequence reads (152). $S_{1C}$, will correspond to the allele of the individual of interest. Some of the sequence reads of $S_{1C}$ (150) may be due to other individuals and some may be distributed among other alleles, e.g. (154). From independent counts of sequence reads from other loci, a system of linear equations may be set up and solved to give an estimate of the proportion of nucleic acids from the individual of interest and other individuals. (For example, two unknowns may be $x_1$=fraction of total sequence reads of genetic marker from the individual of interest and $x_2$=fraction of total sequence reads of genetic marker from other individuals). Distributions of sequence reads among different alleles for each genetic marker can be used to identify the alleles which are characteristic of the individual of interest. A measure of the maximum sensitivity of a clonotype profile measurement (e.g. for detecting a correlating clonotype, such as a leukemia clone) is provided by the value of the largest non-patient allele, as illustrated by line (155) in FIG. 1C. If it is assumed that there is a single contaminating genome with allele, SID, then any clonotype having a value greater than that of SID will be an accurate measurement of a patient clonotype. For any clonotype present in a clonotype profile at a level less than that of the SID allele, there exists a possibility that the clonotype does not originate from the patient.

In one aspect, the invention provides a method for determining a limit of detection of a correlating clonotype in a clonotype profile of a tissue sample comprising T cells and/or B cells of an individual, wherein such method comprises steps: (a) obtaining a tissue sample from an individual, the tissue sample comprising nucleic acids from the individual and possibly from one or more other individuals, the nucleic acids including recombined nucleic acids from T cells and/or B cells and non-recombined nucleic acids; (b) generating a clonotype profile from nucleic acid of the tissue sample: (c) sequencing genetic markers at one or more genetic loci of the nucleic acids from the tissue sample to obtain proportions of the nucleic acid from the one or more other individuals and from the individual based on the genetic identification of the individual and the one or more other individuals from the genetic markers, wherein the genetic markers occur at loci present in both the recombined nucleic acids and the non-recombined nucleic acids; and (d) determining the limit of detection as the level of an allele of any of said genetic markers next highest to that of any allele of the one or more loci of the individual.

Figure 1D:
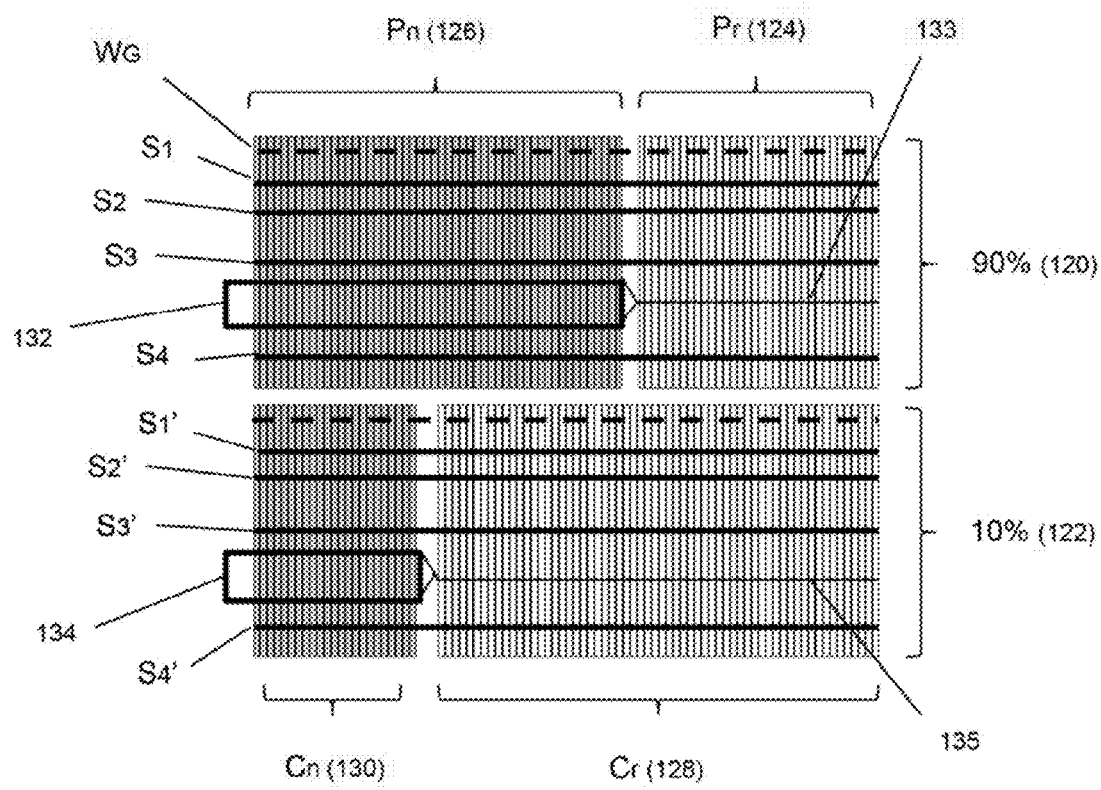
FIG. 1D diagrammatically shows DNA in a sample which comprises non-recombined nucleic acid ($P_o$) and recombined nucleic acid ($P_r$) of a patient and non-recombined nucleic acid ($C_n$) and recombined nucleic acid ($C_r$) contaminating nucleic acids, such as carry over DNA from one or more other patients.

In the some circumstances, the ratio of cell types (and therefore the ratio of recombined DNA to non-recombined DNA) in a tissue sample, such as whole blood or PBMCs, may differ significantly between a sample from a patient, e.g. who is undergoing therapy, such as, cancer chemotherapy, and contamination from another individual, such as a healthy individual. In such cases, further measurements can determine the different fractions of nucleic acid that are derived from different cells from a tissue sample that may include contaminating cells or nucleic acids. In this embodiment, such fractions of nucleic acid may be referred to as patient (or individual of interest) non-recombined ($P_u$), patient recombined ($P_r$), contaminant non-recombined ($C_n$) and contaminant recombined ($C_r$). This aspect of the invention is illustrated in FIG. 1D, which is a diagrammatic representation of the composition of nucleic acid from a tissue sample. Two bands (120) and (122) represent nucleic acid from a patient (or individual of interest) and contaminating nucleic acid, respectively. An exemplary proportion of patient nucleic acid to contaminating nucleic acid may be approximately 90:10. Each band is further divided into recombined nucleic acid ($P_r$ (124) and $C_r$ (128)) and non-recombined nucleic acid ($P_n$ (126) and $C_n$ (130)). As mentioned above, under some circumstances, the ratio $P_n/P_r$ may be very different from the ratio $C_r/C_n$. In each band, genetic marker loci, $S_1$ through $S_4$, are available for determining the ratio of patient nucleic acid to contamination nucleic acid, which is $(P_n+P_r)/(C_n+C_r)=R_{str1}$, where $R_{str1}$ is the ratio of sequence reads of genetic markers from patient nucleic acid to sequence reads of genetic markers from other individuals. i.e. $x_1/x_2$ from above.

The amount or concentration of total nucleic acid in a tissue sample may be determined by comparing the amount of a nucleic acid segment, such as a "house-keeping gene", e.g. GAPDH, common to both recombined and non-recombined nucleic acids (referred to herein as a "common segment"), with one or more internal standards for such segment, or gene. The one or more internal standards are added in known amounts or concentrations to nucleic acid from a tissue sample prior to processing, for example, in a one- or two-stage PCR. Using such a total nucleic acid internal standard, one may obtain a value, Wg, for total nucleic acid in a tissue sample; namely, a value, $W_g=P_r+P_c+C_r+C_n$. Likewise, total amount or concentration of recombined nucleic acid in a tissue sample may be determined by comparing the amount of sequence reads for clonotypes to the amount of sequence reads for one or more recombined sequence internal standards, e.g. V(D)J internal standards, added to nucleic acids from a tissue sample prior to processing. In one embodiment, a set of recombined sequence internal standards are employed that are representative of the immune repertoire being analyzed, particularly in terms of length and composition. In another embodiment, the number of such one or more recombined sequence internal standards may vary between 1 and 10. Using such internal standards, a value, $W_p=C_r+P_r$, may be determined.

Proportions or amounts of non-recombined nucleic acid may be determined by measuring segments of nucleic acid that ordinarily would be excised during the somatic recombination process, i.e. V(D)J recombination, in which TCRs and/or BCRs are assembled. Such segments, referred to herein as "excisable segments," are illustrated in FIG. 1D by boxes (132) and (134) for the patient and contaminating nucleic acids, respectively. One or more of such segments are excised from the recombined nucleic acids as illustrated by lines (133) and (135), indicating the absence of boxes (132) and (134). During V(D)J recombination for both TCRs and BCRs, at least two segments are always excised and lost: a first excised segment between the stretch of genome containing V region genes and the stretch of genome containing D region genes, and a second excised segment between the stretch of genome containing region genes and the stretch of genome containing J region genes. The sequences of these segments are readily obtained from publicly available genome atlases, such as the NCBI Genome Browser (http://www.ncbi.nlm.nih.gov/map), the University of California. Santa Cruz (UCSC) Genome Browser (http://genome.ucsc.edu/cgi-bin/h), or like atlas. For example. V, D, and J-genes that encode human BCRs are found in or near the genomic region 14q32.33; a first excised segment between J genes and D genes has sequence located within coordinates −106,335K to −106,345K on chromosome 14 of the NCBI atlas of the human genome and a second excised segment between D genes and V genes has sequence located between the coordinates −106,406K to −106,385K on chromosome 14 of the NCBI atlas of the human genome. Similar excisable segments exist for V, D, and J-genes that encode human TCRβ chains, which are located on chromosome 7 at 7q32-35, e.g. Hodges et al, J. Clin. Pathol., 56: 1-11 (2003). In one aspect of the invention, the proportion and/or amount of non-recombined nucleic acids, that is, nucleic acids still having the first and second excised segments present, may be determined in at least two ways. Using polymorphic genetic markers located in the excised segments, one may compare the relative amount of nonrecombined nucleic acid from a patient (or individual of interest) and from contaminating nucleic acids. That is, the ratio $P_n/C_u=R_{str2}$ may be computed from sequence reads of genetic markers from the nonrecombined nucleic acids. Alternatively, one may count the total number of nonrecombined sequences using an internal standard. Such an internal standard for the first and/or second excised segments is readily constructed from the above NCBI sequences using conventional techniques, such as discussed more fully below. As for total nucleic acids, such measurement permits the determination of the quantity, $P_n+C_n=W_x$, where $W_x$ is the total number or concentration of nonrecombined nucleic acids.

The above measurements and relationships may be summarized in the following table:

| Measurement | Relationship |
|---|---|
| Total nucleic acid, $W_g$ | $P_r + P_c + C_r + C_n = W_g$ |
| Ratio of genome-wide STRs, $R_{str1}$ | $(P_r + P_c)/(C_r + C_n) = R_{str1}$ |
| Total recombined nucleic acid, $W_p$ | $P_r + C_r = W_p$ |
| Ratio of $1^{st}/2^{nd}$ segment nucleic acid, $R_{str2}$ | $P_n/C_n = R_{str2}$ |
| Total nonrecombined nucleic acid, $W_x$ | $P_n + C_n = W_x$ |

The measurement of recombined nucleic acids may made in two different ways; namely, it may be measured directly using recombined sequence internal standards to give a value Nr=Wp, and it may be measured indirectly using total nucleic acid and total nonrecombined nucleic acid to give a value Nr*=Wg−Wx. The quantity, $z=(Nr*-Nr)/Nr*$, referred to herein as "dark recombination." provides a measure of recombined nucleic acids that are not determined in an assay.

Sequence Tags for Detecting and

Quantifying Clonotype Contamination

In one aspect of the invention, contaminating clonotypes may be detected and quantified by using sequence tags, as an alternative to genetic identity markers. In this aspect, each clonotype in a patient sample is determined by, and labeled with, a sequence tag, as described more fully below. The presence of carry over contamination in the form of clonotypes may be detected by using sequence tags to determine whether a clonotype originated in the current sample or from another sample. This is accomplished by maintaining a record of sequence tags determined from each patient sample, then whenever a subsequent measurement is made the sequence tags of the current measurement are compared to those of prior measurements. Such records of sequence tags associated with clonotypes are conveniently maintained as electronic records on mass storage devices because of the large number of tag from each measurement and the ease of searching and comparing electronic records using conventional algorithms. If a match is found then the most likely cause is carry over contamination, provided that the populations of sequence tags employed in the measurements are sufficiently large. The same exemplary ratios of the size of sequence tag population to a clonotype population for labeling by sampling discussed above are applicable for detecting carry over contamination. In one embodiment, such ratio is 100:1 or greater: in another embodiment, such ratio is 1000:1 or greater.

Determining Clonotypes Using Sequence Tags

In some embodiments, the invention comprises steps for obtaining and analyzing sequence data from a repertoire of immune molecules, such as T cell receptors (TCRs) or B cell receptors (BCRs) or defined fragments thereof, to rapidly and efficiently determine a clonotype profile. Sequence data typically comprises a large collection of sequence reads, i.e. sequences of base calls and associated quality scores, from a DNA sequencer used to analyze the immune molecules. A key challenge in constructing clonotype profiles is to rapidly and accurately distinguish sequence reads that contain genuine differences from those that contain errors from non-biological sources, such as the extraction steps, sequencing chemistry, amplification chemistry, or the like. An aspect of the invention includes attaching a unique sequence tag to each clonotype in a sample to assist in determining whether sequence reads of such conjugates are derived from the same original clonotype. In accordance with one aspect of the invention, sequence tags are attached to the somatically recombined nucleic acid molecules to form tag-molecule conjugates wherein each recombined nucleic acid of such a conjugate has a unique sequence tag. Usually such attachment is made after nucleic acid molecules are extracted from a sample containing T cells and/or B cells. Preferably, such unique sequence tags differ as greatly as possible from one another as determined by conventional distance measures for sequences, such as, a Hamming distance, or the like. By maximizing the distance between sequence tags in tag-molecule conjugates, even with a high rate of sequencing and amplification errors, a sequence tag of a conjugate remains far closer to its ancestral tag sequence than to that of any other tag sequence of a different conjugate. For example, if 16-mer sequence tags are employed and each such tag on a set of clonotypes has a Hamming distance of at least fifty percent, or eight nucleotides, from every other sequence tag on the clonotypes, then at least eight sequencing or amplification errors would be necessary to transform one such tag into another for a mis-read of a sequence tag (and the incorrect grouping of a sequence read of a clonotype with the wrong sequence tag). In one embodiment, sequence tags are selected so that after attachment to recombined nucleic acids molecules to form tag-molecule conjugates, the Hamming distance between tags of the tag-molecule conjugates is a number at least twenty-five percent of the total length of such sequence tags (that is, each sequence tag differs in sequence from every other such tag in at least 25 percent of its nucleotides); in another embodiment, the Hamming distance between such sequence tags is a number at least 50 percent of the total length of such sequence tags.

In one aspect, clonotype profiles are determined by the following steps: (a) obtaining a sample from an individual comprising T-cells and/or B-cells; (b) attaching sequence tags to molecules of recombined nucleic acids of T-cell receptor genes or immunoglobulin genes of the T-cells and/or B-cells to form tag-molecule conjugates, wherein substantially every molecule of the tag-molecule conjugates has a unique sequence tag; (c) amplifying the tag-molecule conjugates: (d) sequencing the tag-molecule conjugates: and (e) aligning sequence reads of like sequence tags to determine sequence reads corresponding to the same clonotypes of the repertoire. Samples containing B-cells or T-cells are obtained using conventional techniques, as described more fully below. In the step of attaching sequence tags, preferably sequence tags are not only unique but also are sufficiently different from one another that the likelihood of even a large number of sequencing or amplification errors transforming one sequence tag into another would be close to zero. After attaching sequence tags, amplification of the tag-molecule conjugate is necessary for most sequencing technologies; however, whenever single-molecule sequencing technologies are employed an amplification step is optional. Single molecule sequencing technologies include, but are not limited to single molecule real-time (SMRT) sequencing, nanopore sequencing, or the like, e.g. U.S. Pat. Nos. 7,313,308; 8,153,375; 7,907,800; 7,960,116; 8.137.569; Manrao et al, Nature Biotechnology, 4(8): 2685-2693 (2012); and the like.

In some embodiments, sequence tags are attached to recombined nucleic acid molecules of a sample by labeling by sampling, e.g. as disclosed by Brenner et al, U.S. Pat. No. 5,846,719: Brenner et al, U.S. Pat. No. 7,537,897: Macevicz, International patent publication WO 2005/111242; and the like, which are incorporated herein by reference. In labeling by sampling, polynucleotides of a population to be labeled (or uniquely tagged) are used to sample (by attachment, linking, or the like) sequence tags of a much larger population. That is, if the population of polynucleotides has K members (including replicates of the same polynucleotide) and the population of sequence tags has N members, then N>>K. In one embodiment, the size of a population of sequence tags used with the invention is at least 10 times the size of the population of clonotypes in a sample; in another embodiment, the size of a population of sequence tags used with the invention is at least 100 times the size of the population of clonotypes in a sample; and in another embodiment, the size of a population of sequence tags used with the invention is at least 1000) times the size of the population of clonotypes in a sample. In other embodiments, a size of sequence tag population is selected so that substantially every clonotype in a sample will have a unique sequence tag whenever such clonotypes are combined with such sequence tag population. e.g. in an attachment reaction, such as a ligation reaction, amplification reaction, or the like. In some embodiments, substantially every clonotype means at least 90 percent of such clonotypes will have a unique sequence tag; in other embodiments, substantially every clonotype means at least 99 percent of such clonotypes will have a unique sequence tag; in other embodiments, substantially every clonotype means at least 99.9 percent of such clonotypes will have a unique sequence tag. In many tissue samples or biopsies the number of T cells or B cells may be up to or about 1 million cells; thus, in some embodiments of the invention employing such samples, the number of unique sequence tags employed in labeling by sampling is at least $10^8$ or in other embodiments at least $10^9$.

In such embodiments, in which up to 1 million clonotypes are labeled by sampling, large sets of sequence tags may be efficiently produced by combinatorial synthesis by reacting a mixture of all four nucleotide precursors at each addition step of a synthesis reaction. e.g. as disclosed in Church, U.S. Pat. No. 5,149,625, which is incorporated by reference. The result is a set of sequence tags having a structure of "$N_1 N_2 \ldots N_k$" where each $N_i$=A, C, G or T and k is the number of nucleotides in the tags. The number of sequence tags in a set of sequence tags made by such combinatorial synthesis is $4^k$. Thus, a set of such sequence tags with k at least 14, or k in the range of about 14 to 18, is appropriate for attaching sequence tags to a $10^6$-member population of molecules by labeling by sampling. Sets of sequence tags with the above structure include many sequences that may introduce difficulties or errors while implementing the methods of the invention. For example, the above combinatorially synthesized set of sequence tags includes many member tags with homopolymers segments that some sequencing approaches, such as sequencing-by-synthesis approaches, have difficulty determining with accuracy above a certain length. Therefore, the invention includes combinatorially synthesized sequence tags having structures that are efficient for particular method steps, such as sequencing. For example, several sequence tag structures efficient for sequencing-by-synthesis chemistries may be made by dividing the four natural nucleotides into disjoint subsets which are used alternatively in combinatorial synthesis, thereby preventing homopolymer segments above a given length. For example, let z be either A or C and x be either G or T, to give a sequence tag structure of:

$$[(z)_1(z)_2 \ldots (z)_i][(x)_i(x)_2 \ldots (x)_j] \ldots$$

where i and j, which may be the same or different, are selected to limit the size of any homopolymer segment. In one embodiment, i and j are in the range of from 1 to 6. In such embodiments, sequence tags may have lengths in the range of from 12 to 36 nucleotides: and in other embodiments, such sequence tags may have lengths in the range of from 12 to 24 nucleotides. In other embodiments other pairing of nucleotides may be used, for example, z is A or T and x is G or C; or z is A or G and x is T or C. Alternatively, let z' be any combination of three of the four natural nucleotides and let x' be whatever nucleotide is not a z' (for example, z' is A, C or G, and x' is T). This gives a sequence tag structure as follows:

$$[(z')_1(z')_2 \ldots (z')_2/x'[(z')_1(z')_2 \ldots (z')_1/x' \ldots$$

where i is selected as above and the occurrence of x' serves as a punctuation to terminate any undesired homopolymers.

A variety of different attachment reactions may be used to attach unique tags to substantially every clonotype in a sample. In one embodiment, such attachment is accomplished by combining a sample containing recombined nucleic acid molecules (which, in turn, comprise clonotype sequences) with a population or library of sequence tags so that members of the two populations of molecules can randomly combine and become associated or linked, e.g. covalently. In such tag attachment reactions, clonotype sequences comprise linear single or double stranded polynucleotides and sequence tags are carried by reagent such as amplification primers, such as PCR primers, ligation adaptors, circularizable probes, plasmids, or the like. Several such reagents capable of carrying sequence tag populations are disclosed in Macevicz, U.S. Pat. No. 8,137,936; Faham et al. U.S. Pat. No. 7,862,999; Landegren et al. U.S. Pat. No. 8,053,188; Unrau and Deugau, Gene, 145: 163-169 (1994); Church, U.S. Pat. No. 5,149,625; and the like, which are incorporated herein by reference.

Figure 1E:
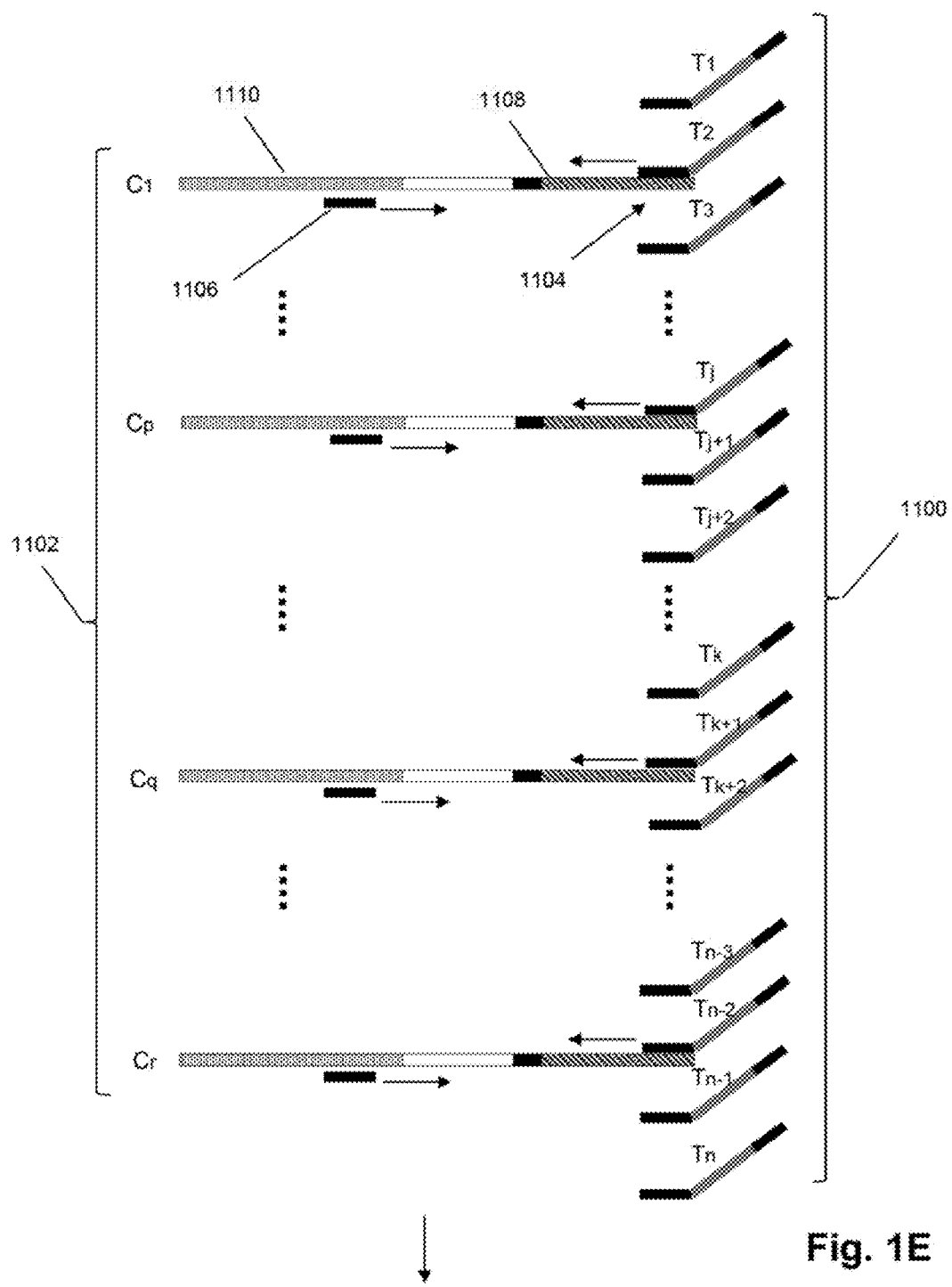
FIGS. 1E-1F illustrate an example of labeling by sampling to attach unique sequence tags to nucleic acid molecules.
Figure 1F:
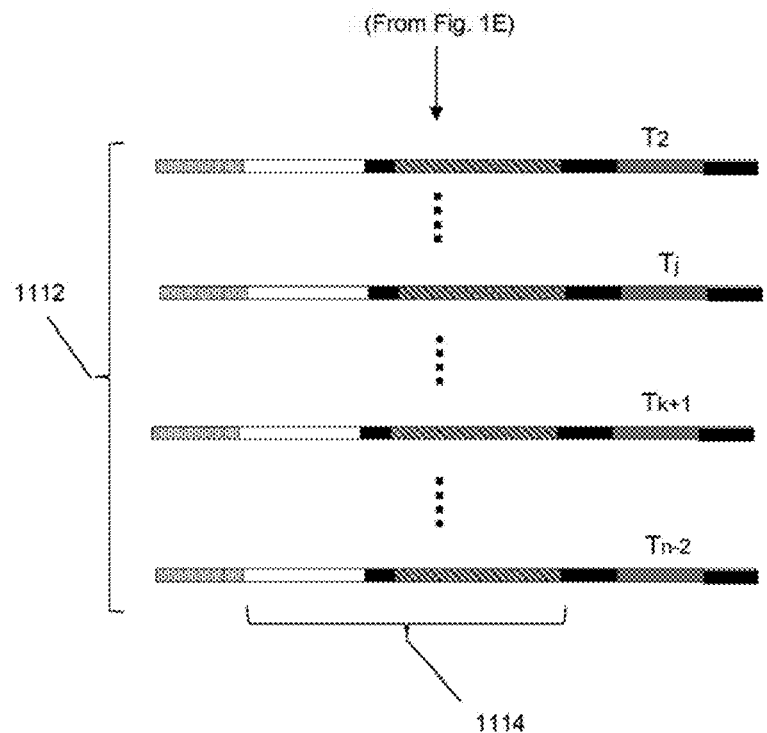

FIGS. 1E and 1F illustrate an attachment reaction comprising a PCR in which a population of sequence tags ($T_1, T_2, T_3 \ldots T_j, T_{j+1} \ldots T_k, T_{k+1} \ldots T_{n-1}, T_n$) is incorporated into primers (1100). The population of sequence tags has a much greater size than that of recombined nucleic acid molecules (1102). The sequence tags are attached to the recombined nucleic acid molecules by annealing the primers to the nucleic acid molecules and extending the primers with a DNA polymerase in the first cycle of a PCR. The figure depicts how the recombined nucleic acid molecules select, or sample, a small fraction of the total population of sequence tags by randomly annealing to the primers by way of their common primer binding regions (1104), for example, in V region (1108). Since the primers (an therefore sequence tags) combine with the recombined nucleic acid sequence molecules randomly, there is a small possibility that the same sequence tag may be attached to different nucleic acid molecules: however, if the population of sequence tags is large as taught herein, then such possibility will be negligibly small so that substantially every recombined nucleic acid molecule will have a unique sequence tag attached. The other primer (1106) of the forward and reverse primer pair anneals to C region (1110) so that after multiple cycles of annealing, extending and melting, amplicon (1112) is formed, thereby attaching unique sequence tags to the V(D)J regions comprising the clonotypes of population (1102). That is, amplicon (1112) comprises the tag-molecule conjugates from the attachment reaction.

Such immune molecules typically form an immune repertoire which comprises a very large set of very similar polynucleotides (e.g. >1000, but more usually from 100,000 to 1,000,000, or more) which are relatively short in length (e.g. usually less than 30 bp). In one aspect of the invention, the inventors recognized and appreciated that these characteristics permitted the use of highly dissimilar sequence tags to efficiently compare sequence reads of highly similar clonotypes to determine whether they are derived from the same original sequence or not.

Figure 1G:
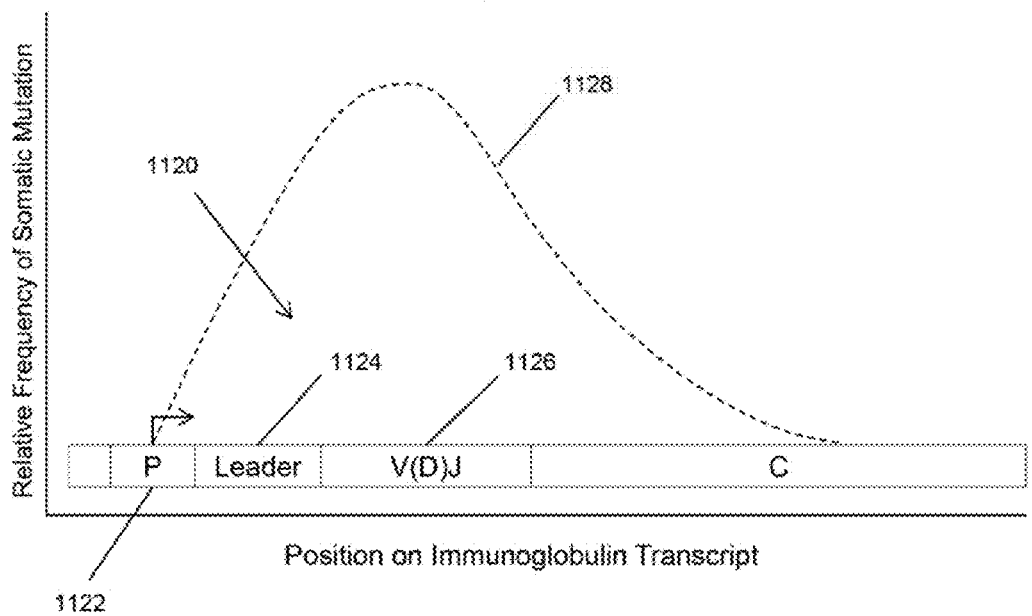
FIG. 1G illustrates an IgH transcript and sources of natural variability within it.

The complexity of immune repertoires is well-known. e.g. Arstila et al, Science, 286: 958-96 (1999) and Warren et al (cited above). FIG. 1G illustrates diagrammatically a typical transcript of an IgH molecule (1120) from which a clonotype profile is derived in accordance with some embodiments of the invention. Sources of natural sequence variability include modular recombination of the C, D, J and V segments from large sets carried by the genome, nucleotide additions and deletions to the ends of the D segment to produce the so-called "NDN" regions, and somatic hypermutation where substitutions are made randomly over the length of transcript (1122) at a relative frequency roughly as indicated by curve (1128). In one aspect of the invention, complex populations of such IgH and TCR transcripts are amplified and sequenced. In one aspect one or both operations for IgH molecules are carried out by using redundant primers annealing to different sites in the V regions (described more fully below). This is particularly advantageous where a sequencing chemistry is employed that has a relatively high error rate or where such sequence variability is difficult or impossible to know beforehand. In the latter case, primer extension for amplification or generation of sequence reads takes place even if one or more primer binding sites are inoperable, or substantially inoperable, because of mismatches caused (for example) by one or more somatic mutations. Starting from promoter P (1122) relative frequency shown by curve (1128) climbs through leader region (1124) to a maximum over the V(D)J region (1126) of the transcript after which it drop to near zero. In one aspect of the invention, a segment of recombined B cell nucleic acid is amplified by a PCR with a plurality of forward primers or a plurality of reverse primers to generate a nested set of templates, e.g. as disclosed in Faham and Willis. U.S. patent publication 2011/0207134. Templates from such a set may be further amplified on a surface to form separate amplicons (e.g. by bridge PCR using a cBot instrument, Illumina, San Diego, Calif.). Templates from the same nested set may be associated with one another by sequence reads generated at their common ends. Nested sets of templates allow a sequencing chemistry with relative high error rates to be used to analyze longer sequences than otherwise would be possible, while at the same time maintaining high average quality scores over the entire length of the sequence. The nested sets also ensure that at least one sequence read is obtained from a V region even if it has been subjected to somatic hypermutation.

Figure 5:
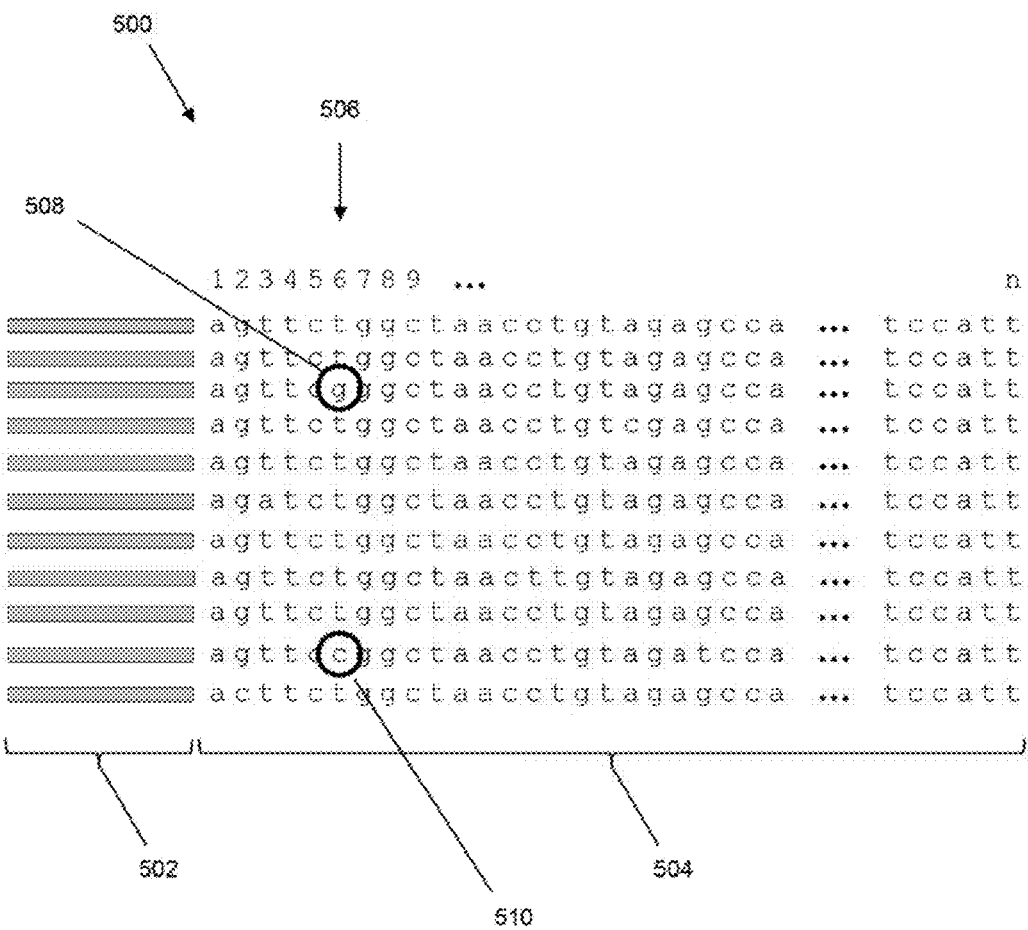
FIG. 5 illustrates one implementation of the step of determining the sequence of a clonotype from sequence reads associated with the same sequence tag.

Somatic mutations in IgH molecules add a layer of difficulty in reconstructing clonotypes from sequence read data, because of the difficulty in determining whether a base change is due to sequencing or amplification error or is due to a natural mutation process. The use of sequence tags in accordance with the invention greatly mitigates such difficulties because every nucleic acid encoding an IgH will receive a distinct and unique sequence tag. As illustrated in FIG. 5, sequence reads (500) pursuant to the invention each comprise a copy of a sequence tag (502) and a copy of a clonotype (504). All sequence reads having the same sequence tag are assembled so that the nucleotides of each position in the clonotype portion can be compared. Thus, even if IgH-encoding sequences differ by no more than a single base, they will receive a distinct sequence tag, so that closely related IgH-encoding nucleic acids in a sample are not compared with one another in the clonotype determination process. As mentioned above, errors in the sequence tags are not significant because the sequences of the sequence tags associated with clonotypes are so far apart in sequence space that a huge number of base changes could be sustained without one sequence tag becoming close in sequence space to any other sequence tag.

Constructing clonotypes from sequence read data depends in pan on the sequencing method used to generate such data, as the different methods have different expected read lengths and data quality. In one approach, a Solexa sequencer is employed to generate sequence read data for analysis. In one embodiment, a sample is obtained that provides at least 0.5-1.0×10⁶ lymphocytes to produce at least 1 million template molecules, which after optional amplification may produce a corresponding one million or more clonal populations of template molecules (or clusters). For most high throughput sequencing approaches, including the Solexa approach, such over sampling at the cluster level is desirable so that each template sequence is determined with a large degree of redundancy to increase the accuracy of sequence determination. For Solexa-based implementations, preferably the sequence of each independent template is determined 10 limes or more. For other sequencing approaches with different expected read lengths and data quality, different levels of redundancy may be used for comparable accuracy of sequence determination. Those of ordinary skill in the art recognize that the above parameters, e.g. sample size, redundancy, and the like, are design choices related to particular applications.

Figure 2A:
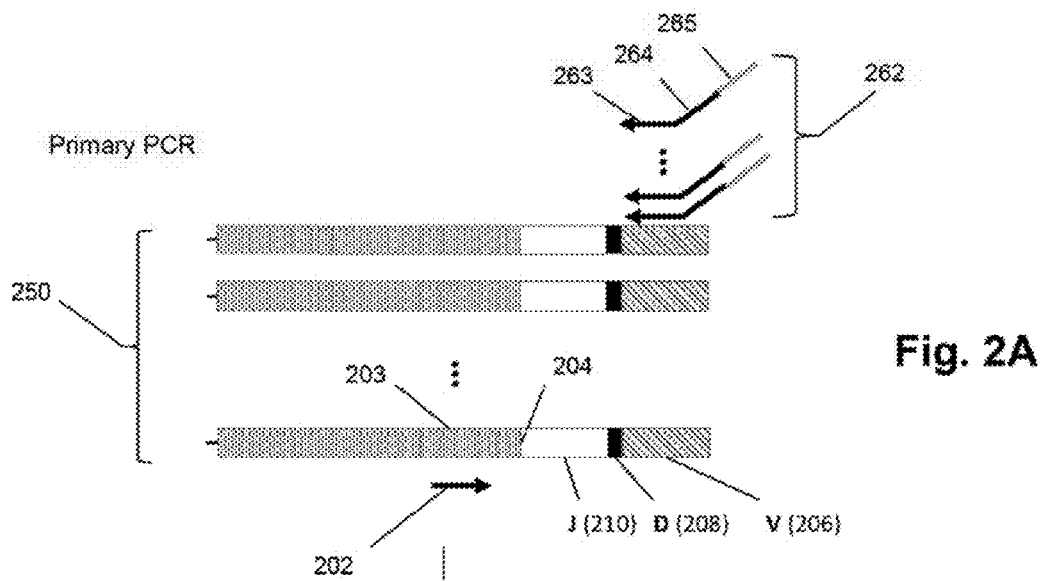
FIGS. 2A-2C show a two-staged PCR scheme for amplifying TCRβ genes.
Figure 2B:
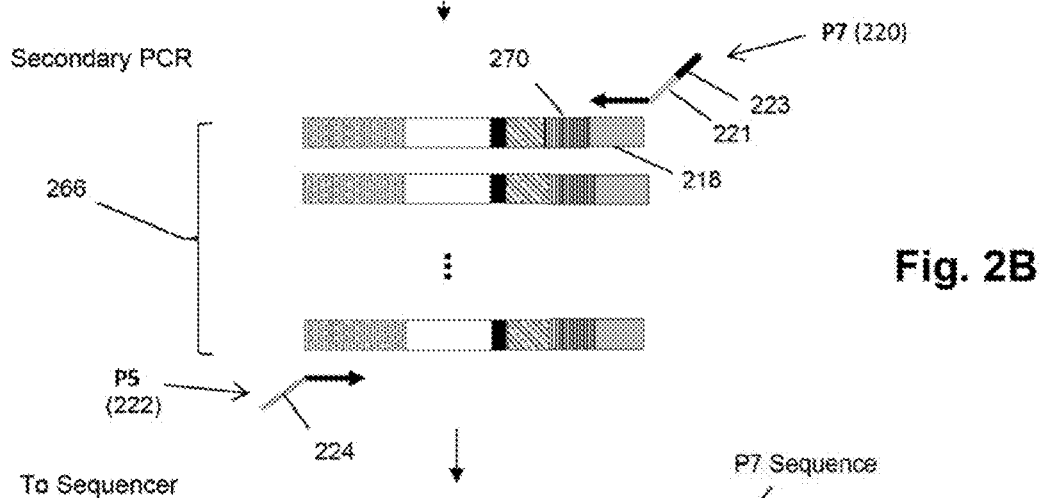
Figure 2C:
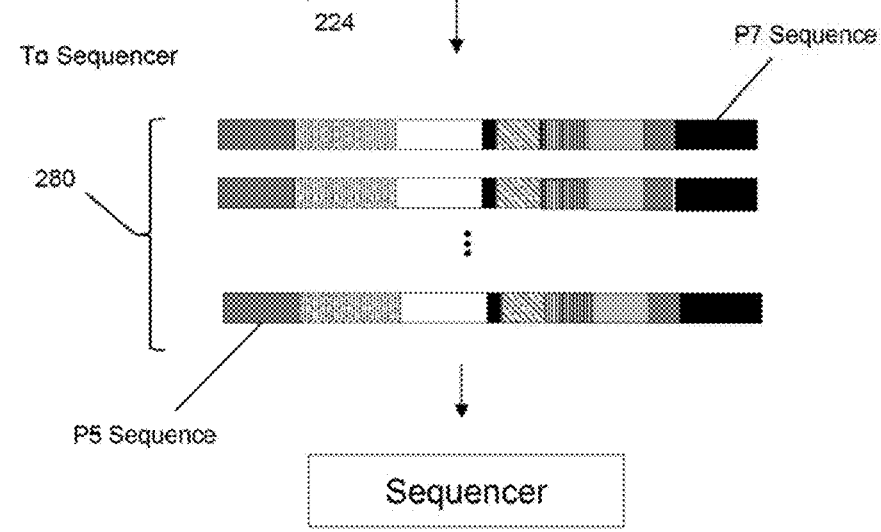

FIGS. 2A-2C illustrate exemplary steps of attaching unique sequence tags to recombined nucleic acid molecules in a two stage PCR. Population of recombined nucleic acid molecules (250) from a sample containing T-cells or B-cells are combined in a PCR mixture with forward and reverse primers (202) and (262). Primers (262) each comprise three regions: target annealing region (263) (which in this illustration is V region (206)); sequence tag (264); and primer binding region (265) for the second stage of the two-stage PCR. In this illustration, primers (262) comprise a mixture of target annealing regions to account for the diversity of V region sequence. Thus, every different primer is prepared with a sequence tag region. Alternatively, the sequence tag element may be attached to C region primer (202) along with a primer binding region for the second PCR stage. As noted, recombined nucleic acid molecules (250) comprise constant, or C, region (203), J region (210), D region (208), and V region (206), which may represent a V(D)J segment encoding a CDR3 region of either a TCR or immunoglobulin. After a few cycles, for example, 4 to 10, first stage amplicon (266) is produced with each member polynucleotide including sequence tag (270). In the second stage PCR, polynucleotides of amplicon (266) are reamplified with new forward and reverse primers P5 (222) and P7 (220) which add further primer binding sites (224) and (223) for cluster formation using bridge PCR in a Solexa/Illumina sequencer. Primer P7 also include a secondary sequence tag (221) for optional multiplexing of samples in a single sequencing run. After the secondary PCR amplicon (280) is produced with embedded P5 and P7 sequences by which bridge PCR may be carried out.

Further Sequence Tags

The invention uses methods of labeling nucleic acids, such as fragments of genomic DNA, with unique sequence tags, which may include "mosaic tags,"prior to amplification and sequencing. Such sequence tags are useful for identifying amplification and sequencing errors. Mosaic tags minimize sequencing and amplification artifacts due to inappropriate annealing , priming, hairpin formation, or the like, that may occur with completely random sequence tags of the prior art. In one aspect, mosaic tags are sequence tags that comprise alternating constant regions and variable regions, wherein each constant region has a position in the mosaic tag and comprises a predetermined sequence of nucleotides and each variable region has a position in the mosaic tag and comprises a predetermined number of randomly selected nucleotides. By way of illustration, a 22-mer mosaic tag (SEQ ID NO: 1) may have the following form:

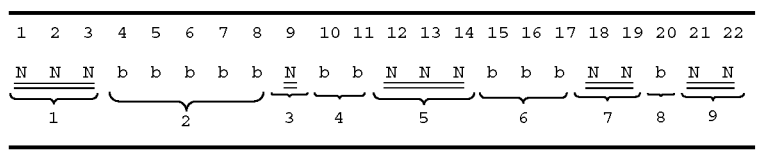

There are nine constant and variable regions, with regions 1 (nucleotides 1-3), 3 (nucleotide 9), 5(nucleotides 12-14), 7 (nucleotides 18-19) and 9 (nucleotides 21-22) being variable (double underlined nucleotides) and regions 2 (nucleotides 4-8), 4 (nucleotides 10-11), 6 (nucleotides 15-17), and 8 (nucleotide 20) being constant. N represents a randomly selected nucleotide from the set of A, C, G or T; thus, the number of mosaic tags of this example is $4^8=4,194,304$ tags. b represents a predetermined nucleotide al the indicated position. In some embodiments. the sequence of b's, "***bbbbb*bb*bbbb**", is selected to minimize the likelihood of having a perfect match in a genome of the organism making up the sample.

In one aspect, for mosaic tags of a particular embodiment of the method of the invention, all constant regions with the same position have the same length and all variable regions with the same position have the same length. This allows mosaic tags to be synthesized using partial combinatorial synthesis with conventional chemistries and instruments.

In one aspect, mosaic tags comprise from 10 to 100 nucleotides, or from 12 to 80 nucleotides, or from 15 to 60 nucleotides. In some embodiments, mosaic tags comprise at least eight nucleotide positions with randomly selected nucleotides; in other embodiments, whenever mosaic tags have a length of at least 15 nucleotides, they comprise at least 12 nucleotide positions with randomly selected nucleotides. In another aspect, no variable region within a mosaic tag may have a length that is greater than seven nucleotides.

In another aspect, mosaic tags may be used in the following steps: (i) preparing DNA templates from nucleic acids in a sample; (ii) labeling by sampling the DNA templates to form a multiplicity tag-template conjugates, wherein substantially every DNA template of a tag-template conjugate has a unique mosaic tag comprising alternating constant regions and variable regions, each constant region having a position in the mosaic tag and a length of from 1 to 10 nucleotides of a predetermined sequence and each variable region having a position in the mosaic tag and a length of from 1 to 10 randomly selected nucleotides, such that constant regions having the same positions have the same lengths and variable region having the same positions have the same lengths: (iii) amplifying the multiplicity of tag-template conjugates; (iv) generating a plurality of sequence reads for each of the amplified tag-template conjugates; and (v) determining a nucleotide sequence of each of the nucleic acids by determining a consensus nucleotide at each nucleotide position of each plurality of sequence reads having identical mosaic tags. In another aspect, mosaic tags may be used in the following steps: (a) preparing single stranded DNA templates from nucleic acids in a sample; (b) labeling by sampling the single stranded DNA templates to form tag-template conjugates, wherein substantially every single stranded DNA template of a tag-template conjugate has a unique sequence tag (that is, a mosaic tag) having a length of at least 15 nucleotides and having the following form:

$$[(N_1N_2\ldots N_{Kj})(b_1b_2\ldots b_{Lj})]_M$$

wherein each $N_i$, for i=1, 2, ... $K_j$, is a nucleotide randomly selected from the group consisting of A, C, G and T; $K_j$ is an integer in the range of from 1 to 10 for each j less than or equal to M (that is, regions $N_1N_2\ldots N_{Kj}$ are variable regions): each $b_i$, for i=1, 2, ... $L_j$, is a nucleotide; $L_j$ is an integer in the range of from 1 to 10 for each j less than or equal to M; such that every sequence tag (i) has the same Kj for every j and (ii) has the same sequences $b_1b_2\ldots b_{Lj}$ for every j (that is, regions $b_1b_2\ldots b_{Lj}$ are constant regions); and M is an integer greater than or equal to 2; (c) amplifying the tag-template conjugates; (d) generating a plurality of sequence reads for each of the amplified tag-template conjugates, and (e) determining a nucleotide sequence of each of the nucleic acids by determining a consensus nucleotide at each nucleotide position of each plurality of sequence reads having identical sequence tags. In some embodiments, the plurality of sequence reads is at least $10^4$; in other embodiments, the plurality of sequence reads is at least $10^5$: in still other embodiments, the plurality of sequence reads is at least $10^6$. In some embodiments, the total length of the above sequence tag is in the range of from 15 to 80 nucleotides.

Determining Clonotypes from Sequence Reads Using Sequence Tags accordance with one aspect of the invention, clonotypes of a sample are determined by first grouping sequence reads based on their sequence tags. Such grouping may be accomplished by conventional sequence alignment methods. Guidance for selecting alignment methods is available in Batzoglou, Briefings in , 6: 6-22 (2005), which is incorporated by reference. After sequence reads are assembled in groups corresponding to unique sequence tags, then the sequences of the associated clonotypes may be analyzed to determine the sequence of the clonotype from the sample. Fig, 5 illustrates an exemplary alignment and method from determining the sequence (SEQ ID NO: 2) of a clonotype associated with a unique sequence tag. In this example, eleven sequence reads (500) are aligned by way of their respective sequence tags (502) after which nucleotides at each position of the clonotype portions of the sequence reads, indicated as 1, 2, 3, 4, . . . n, are compared. For example, nucleotides at position 6 (506) are t, t, g, t, t, t, t, t, t, c, t; that is, nine base calls are t's, one "g" (508) and one is "c" (510) (SEQ ID NO: 3 and SEQ ID NO: 4). In one embodiment, the correct base call of the clonotype sequence at a position is whatever the identity of the majority base is. In the example of position 6 (506), the base call is "t", because it is the nucleotide in the majority of sequence reads at that position. In other embodiments, other factors may be taken into account to determine a correct base call for a clonotype sequence, such as quality scores of the base calls of the sequence reads, identities of adjacent bases, or the like Once clonotypes are determined as described above, a clonotype profile comprising the abundances or frequencies of each different clonotype of a sample may be assembled.

Samples

Clonotype profiles are obtained from samples of immune cells, which are present in a wide variety of tissues. Immune cells of interest include T-cells and/or B-cells. T-cells (T lymphocytes) include, for example, cells that express T cell receptors (TCRs). B-cells (B lymphocytes) include, for example, cells that express B cell receptors (BCRs). T-cells include helper T cells (effector T cells or Th cells), cytotoxic T cells (CTLs), memory T cells, and regulatory T cells, which may be distinguished by cell surface markers. In one aspect a sample of T cells includes at least 1,000T cells; but more typically, a sample includes at least 10,000 T cells, and more typically, at least 100,000 T cells. In another aspect, a sample includes a number of T cells in the range of from 1000 to 1,000,000 cells. A sample of immune cells may also comprise B cells. B-cells include, for example, plasma B cells, memory B cells, B1 cells, B2 cells, marginal-zone B cells, and follicular B cells. B-cells can express immunoglobulins (also referred to as antibodies or B cell receptors). As above, in one aspect a sample of B cells includes at least 1,000 B cells; but more typically, a sample includes at least 10,000 B cells, and more typically, at least 100,000 B cells. In another aspect, a sample includes a number of B cells in the range of from 1000 to 1,000,000 B cells.

Samples (sometimes referred to as "tissue samples") used in the methods of the invention can come from a variety of tissues, including, for example, tumor tissue, blood and blood plasma, lymph fluid, cerebrospinal fluid surrounding the brain and the spinal cord, synovial fluid surrounding bone joints, and the like. In one embodiment, the sample is a blood sample. The blood sample can be about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 mL. The sample can be a tumor biopsy. The biopsy can be from, for example, from a tumor of the brain, liver, lung, heart, colon, kidney, or bone marrow. Any biopsy technique used by those skilled in the art can be used for isolating a sample from a subject. For example, a biopsy can be an open biopsy, in which general anesthesia is used. The biopsy can be a closed biopsy, in which a smaller cut is made than in an open biopsy. The biopsy can be a core or incisional biopsy, in which part of the tissue is removed. The biopsy can be an excisional biopsy, in which attempts to remove an entire lesion are made. The biopsy can be a fine needle aspiration biopsy, in which a sample of tissue or fluid is removed with a needle.

A sample or tissue sample includes nucleic acid, for example, DNA (e.g., genomic DNA) or RNA (e.g., messenger RNA). The nucleic acid can be cell-free DNA or RNA, e.g. extracted from the circulatory system, Vlassov et al, Curr. Mol. Med., 10: 142-165 (2010); Swarup et al, FEBS Lett., 581: 795-799 (2007). In the methods of the invention, the amount of RNA or DNA from a subject that can be analyzed includes varies widely. For example. DNA or RNA of a single cell may be all that is required for a calibration test (i.e. an initial measurement to determine a correlating clonotype for a disease). For generating a clonotype profile, sufficient nucleic acid must be in a sample to obtain a useful representation of an individual's immune receptor repertoire. More particularly, for generating a clonotype profile from genomic DNA at least 1 ng of total DNA from T cells or B cells (i.e. about 30) diploid genome equivalents) is extracted from a sample; in another embodiment, at least 2 ng of total DNA (i.e. about 600 diploid genome equivalents) is extracted from a sample; and in another embodiment, at least 3 ng of total DNA (i.e. about 900 diploid genome equivalents) is extracted from a sample. One of ordinary skill would recognize that as the fraction of lymphocytes in a sample decreases, the foregoing minimal amounts of DNA must increase in order to generate a clonotype profile containing more than about 1000) independent clonotypes. For generating a clonotype profile from RNA, in one embodiment, a sufficient amount of RNA is extracted so that at least 1000 transcripts are obtained which encode distinct TCRs, BCRs, or fragments thereof. The amount of RNA that corresponds to this limit varies widely from sample to sample depending on the fraction of lymphocytes in a sample, developmental stage of the lymphocytes, and the like. In one embodiment, at least 100 ng of RNA is extracted from a tissue sample containing B cells and/or T cells for the generating of a clonotype profile: in another one embodiment, at least 500 ng of RNA is extracted from a tissue sample containing B cells and/or T cells for the generating of a clonotype profile. RNA used in methods of the invention may be either total RNA extracted from a tissue sample or polyA RNA extracted directly from a tissue sample or from total RNA extracted from a tissue sample. The above nucleic acid extractions may be carried out using commercially available kits, e.g. from Invitrogen (Carlsbad, Calif.), Qiagen (San Diego, Calif.), or like vendors. Guidance for extracting RNA is found in Liedtke et al. PCR Methods and Applications, 4: 185-187 (1994); and like references.

As discussed more fully below (Definitions), a sample containing lymphocytes is sufficiently large so that substantially every T cell or B cell with a distinct clonotype is represented therein, thereby forming a repertoire (as the term is used herein). In one embodiment, a sample is taken that contains with a probability of ninety-nine percent every clonotype of a population present at a frequency of 0.001 percent or greater. In another embodiment, a sample is taken that contains with a probability of ninety-nine percent every clonotype of a population present at a frequency of 0.0001 percent or greater. In one embodiment, a sample of B cells or T cells includes at least a half million cells, and in another embodiment such sample includes at least one million cells.

Whenever a source of material from which a sample is taken is scarce, such as, clinical study samples, or the like. DNA from the material may be amplified by a non-biasing technique, such as whole genome amplification (WGA), multiple displacement amplification (MDA); or like technique, e.g. Hawkins et al, Curr. Opin. Biotech., 13: 65-67 (2002); Dean et al, Genome Research, 11: 1095-1099 (2001); Wang et al, Nucleic Acids Research, 32: e76 (2004): Hosono et al. Genome Research, 13: 954-964 (2003); and the like.

Blood samples are of particular interest and may be obtained using conventional techniques, e.g. Innis et al. editors, PCR Protocols (Academic Press, 1990); or the like. For example, white blood cells may be separated from blood samples using convention techniques. e.g. RosetteSep kit (Stem Cell Technologies, Vancouver. Canada). Likewise, other fractions of whole blood, such as peripheral blood mononuclear cells (PBMCs) may be isolated for use with methods of the invention using commercially available kits. e.g. Miltenyi Biotec, Auburn. CA), or the like. Blood samples may range in volume from 100 µL to 10 mL; in one aspect, blood sample volumes are in the range of from 200 100 µL to 2 mL. DNA and/or RNA may then be extracted from such blood sample using conventional techniques for use in methods of the invention. e.g. DNeasy Blood & Tissue Kit (Qiagen. Valencia, Calif.). Optionally, subsets of white blood cells, e.g. lymphocytes, may be further isolated using conventional techniques, e.g. fluorescently activated cell sorting (FACS) (Becton Dickinson, San Jose, Calif.), magnetically activated cell sorting (MACS) (Miltenyi Biotec, Auburn, Calif.), or the like.

In some embodiments, recombined nucleic acids are present in the DNA of each individual's adaptive immunity cells as well as their associated RNA transcripts, so that either RNA or DNA can be sequenced in the methods of the provided invention. A recombined sequence from a T-cell or B-cell encoding a T cell receptor or immunoglobulin molecule, or a portion thereof, is referred to as a clonotype. The DNA or RNA can correspond to sequences from T-cell receptor (TCR) genes or immunoglobulin (Ig) genes that encode antibodies. For example, the DNA and RNA can correspond to sequences encoding $\alpha$, $\beta$, $\gamma$, or $\delta$ chains of a TCR. In a majority of T-cells, the TCR is a heterodimer consisting of an $\alpha$-chain and $\beta$-chain. The TCR$\alpha$ chain is generated by VJ recombination, and the $\beta$ chain receptor is generated by V(D)J recombination. For the TCR$\beta$ chain, in humans there are 48 V segments, 2 D segments, and 13 J segments. Several bases may be deleted and others added (called N and P nucleotides) at each of the two junctions. In a minority of T-cells, the TCRs consist of $\gamma$ and 6 delta chains. The TCR $\gamma$ chain is generated by VJ recombination, and the TCR $\delta$ chain is generated by V(D)J recombination (Kemnneth Murphy, Paul Travers, and Mark Walport. *Janeway's Immunology* 7th edition, Garland Science, 2007, which is herein incorporated by reference in its entirety).

The DNA and RNA analyzed in the methods of the invention can correspond to sequences encoding heavy chain immunoglobulins (IgH) with constant regions ($\alpha$, $\delta$, $\epsilon$, $\gamma$, or $\mu$) or light chain immunoglobulins (IgK or IgL) with constant regions $\lambda$ or $\kappa$. Each antibody has two identical light chains and two identical heavy chains. Each chain is composed of a constant (C) and a variable region. For the heavy chain, the variable region is composed of a variable (V), diversity (D), and joining (J) segments. Several distinct sequences coding for each type of there segments are present in the genome. A specific VDJ recombination event occurs during the development of a B-cell, marking that cell to generate a specific heavy chain. Diversity in the light chain is generated in a similar fashion except that there is no D region so there is only VJ recombination. Somatic mutation often occurs close to the site of the recombination, causing the addition or deletion of several nucleotides, further increasing the diversity of heavy and light chains generated by B-cells. The possible diversity of the antibodies generated by a B-cell is then the product of the different heavy and light chains. The variable regions of the heavy and light chains contribute to form the antigen recognition (or binding) region or site. Added to this diversity is a process of somatic hypermutation which can occur after a specific response is mounted against some epitope.

In accordance with the invention, primers may be selected to generate amplicons of subsets of recombined nucleic acids extracted from lymphocytes. Such subsets may be referred to herein as "somatically rearranged regions." Somatically rearranged regions may comprise nucleic acids from developing or from fully developed lymphocytes, where developing lymphocytes are cells in which rearrangement of immune genes has not been completed to form molecules having full V(D)J regions. Exemplary incomplete somatically rearranged regions include incomplete IgH molecules (such as, molecules containing only D-J regions), incomplete TCRδ molecules (such as, molecules containing only D-J regions), and inactive IgK (for example, comprising Kde-V regions).

Adequate sampling of the cells is an important aspect of interpreting the repertoire data, as described further below in the definitions of "clonotype" and "repertoire." For example, starting with 1,000 cells creates a minimum frequency that the assay is sensitive to regardless of how many sequencing reads are obtained. Therefore one aspect of this invention is the development of methods to quantitate the number of input immune receptor molecules. This has been implemented this for TCRβ and IgH sequences. In either case the sate set of primers are used that are capable of amplifying all the different sequences. In order to obtain an absolute number of copies, a real time PCR with the muliplex of primers is performed along with a standard with a known number of immune receptor copies. This real time PCR measurement can be made from the amplification reaction that will subsequently be sequenced or can be done on a separate aliquot of the same sample. In the case of DNA, the absolute number of rearranged immune receptor molecules can be readily converted to number of cells (within 2 fold as some cells will have 2 rearranged copies of the specific immune receptor assessed and others will have one). In the case of cDNA the measured total number of rearranged molecules in the real time sample can be extrapolated to define the total number of these molecules used in another amplification reaction of the same sample. In addition, this method can be combined with a method to determine the total amount of RNA to define the number of rearranged immune receptor molecules in a unit amount (say 1 μg) of RNA assuming a specific efficiency of cDNA synthesis. If the total amount of cDNA is measured then the efficiency of cDNA synthesis need not be considered. If the number of cells is also known then the rearranged immune receptor copies per cell can be computed. If the number of cells is not known, one can estimate it from the total RNA as cells of specific type usually generate comparable amount of RNA. Therefore from the copies of rearranged immune receptor molecules per 1 μg one can estimate the number of these molecules per cell.

One disadvantage of doing a separate real time PCR from the reaction that would be processed for sequencing is that there might be inhibitory effects that are different in the real time PCR from the other reaction as different enzymes, input DNA, and other conditions may be utilized. Processing the products of the real time PCR for sequencing would ameliorate this problem. However low copy number using real time PCR can be due to either low number of copies or to inhibitory effects, or other suboptimal conditions in the reaction.

Known amounts of one or more internal standards to cDNA or genomic DNA can be added to an assay reaction to determine absolute quantities or concentrations of cDNA or genomic DNA samples of unknown quantity. By counting the number of molecules of the internal standard and comparing it to the rest of the sequences of the same sample, one can estimate the number of rearranged immune receptor molecules in the initial cDNA sample. (Such techniques for molecular counting are well-known, e.g. Brenner et al., U.S. Pat. No. 7,537,897, which is incorporated herein by reference).

Amplification of Nucleic Acid Populations

Amplicons of target populations of nucleic acids, particularly recombined immune molecules, may be generated by a variety of amplification techniques. In one aspect of the invention, multiplex PCR is used to amplify members of a mixture of recombined immune molecules, such as T cell receptors or portions thereof or B cell receptors or portions thereof. Guidance for carrying out multiplex PCRs of such immune molecules is found in the following references, which are incorporated by reference: Morley, U.S. Pat. No. 5,296,351; Gorski, U.S. Pat. No. 5,837,447; Dau. U.S. Pat. No. 6,087,096; Von Dongen et al. U.S. patent publication 2006/2342334; European patent publication EP 1544308B1: and the like. In some embodiments of the invention, a step of generating a clonotype profile include steps of (a) amplifying a portion of T cell receptor genes and/or a portion of B cell receptor genes and (b) sequencing nucleic acids of the resulting amplicon. As explained elsewhere, the number of amplicon nucleic acids sequenced may vary from application to application. For example, a clonotype profile to determine whether a leukemia patient is still in remission will be large so that the limit of detection of any tumor clones will be very low. In some embodiments, the number of amplicon nucleic acids sequenced is at least 1000; in other embodiments, the number of amplicon nucleic acids sequenced is at least $10^4$; in other embodiments, the number of amplicon nucleic acids sequenced is at least $10^5$. Such a generating step may also include further steps of coalescing sequence reads into clonotypes, enumerating or tabulating clonotypes, forming frequency distributions of clonotypes, identifying related subsets of clonotypes, displaying clonotype frequency information, and the like.

After amplification of DNA from the genome (or amplification of nucleic acid in the form of cDNA by reverse transcribing RNA), the individual nucleic acid molecules can be isolated, optionally re-amplified, and then sequenced individually. Exemplary amplification protocols may be found in van Dongen et al, Leukemia, 17: 2257-2317 (2003) or van Dongen et al, U.S. patent publication 2006/0234234, which is incorporated by reference. Briefly, an exemplary protocol is as follows: Reaction buffer: ABI Buffer II or ABI Gold Buffer (Life Technologies, San Diego. CA); 50 μL final reaction volume: 100 ng sample DNA; 10 pmol of each primer (subject to adjustments to balance amplification as described below); dNTPs at 200 μM final concentration; $MgCl_2$ at 1.5 mM final concentration (subject to optimization depending on target sequences and polymerase); Taq polymerase (1-2 U/tube); cycling conditions: reactivation 7 min at 95° C.; annealing at 60° C.; cycling times: 30s denaturation; 30s annealing; 30s extension. Polymerases that can be used for amplification in the methods of the invention are commercially available and include, for example, Taq polymerase, AccuPrime polymerase, or Pfu. The choice of polymerase to use can be based on whether fidelity or efficiency is preferred.

Real time PCR, picogreen staining, nanofluidic electrophoresis (e.g. LabChip) or UV absorption measurements can be used in an initial step to judge the functional amount of amplifiable material.

In one aspect, multiplex amplifications are carried out so that relative amounts of sequences in a starting population are substantially the same as those in the amplified population, or amplicon. That is, multiplex amplifications are carried out with minimal amplification bias among member sequences of a sample population. In one embodiment, such relative amounts are substantially the same if each relative amount in an amplicon is within five fold of its value in the starting sample. In another embodiment, such relative amounts are substantially the same if each relative amount in an amplicon is within two fold of its value in the starting sample. As discussed more fully below, amplification bias in PCR may be detected and corrected using conventional techniques so that a set of PCR primers may be selected for a predetermined repertoire that provide unbiased amplification of any sample.

In regard to many repertoires based on TCR or BCR sequences, a multiplex amplification optionally uses all the V segments. The reaction is optimized to attempt to get amplification that maintains the relative abundance of the sequences amplified by different V segment primers. Some of the primers are related, and hence many of the primers may "cross talk," amplifying templates that are not perfectly matched with it. The conditions are optimized so that each template can be amplified in a similar fashion irrespective of which primer amplified it. In other words if there are two templates, then after 1,000 fold amplification both templates can be amplified approximately 1,000 fold, and it does not matter that for one of the templates half of the amplified products carried a different primer because of the cross talk. In subsequent analysis of the sequencing data the primer sequence is eliminated from the analysis, and hence it does not matter what primer is used in the amplification as long as the templates are amplified equally.

In one embodiment, amplification bias may be avoided by carrying out a two-stage amplification (as described in Faham and Willis, cited above) wherein a small number of amplification cycles are implemented in a first, or primary, stage using primers having tails non-complementary with the target sequences. The tails include primer binding sites that are added to the ends of the sequences of the primary amplicon so that such sites are used in a second stage amplification using only a single forward primer and a single reverse primer, thereby eliminating a primary cause of amplification bias. Preferably, the primary PCR will have a small enough number of cycles (e.g. 5-10) to minimize the differential amplification by the different primers. The secondary amplification is done with one pair of primers and hence the issue of differential amplification is minimal. One percent of the primary PCR is taken directly to the secondary PCR. Thirty-five cycles (equivalent to ~28 cycles without the 100 fold dilution step) used between the two amplifications were sufficient to show a robust amplification irrespective of whether the breakdown of cycles were: one cycle primary and 34 secondary or 25 primary and 10 secondary. Even though ideally doing only 1 cycle in the primary PCR may decrease the amplification bias, there are other considerations. One aspect of this is representation. This plays a role when the starting input amount is not in excess to the number of reads ultimately obtained. For example, if 1,000,000 reads are obtained and starting with 1,000,000 input molecules then taking only representation from 100,000) molecules to the secondary amplification would degrade the precision of estimating the relative abundance of the different species in die original sample. The 100 fold dilution between the 2 steps means that the representation is reduced unless the primary PCR amplification generated significantly more than 100 molecules. This indicates that a minimum 8 cycles (256 fold), but more comfortably 10 cycle (~1,000 fold), may be used. The alternative to that is to take more than 1% of the primary PCR into the secondary but because of the high concentration of primer used in the primary PCR, a big dilution factor is can be used to ensure these primers do not interfere in the amplification and worsen the amplification bias between sequences. Another alternative is to add a purification or enzymatic step to eliminate the primers from the primary PCR to allow a smaller dilution of it. In this example, the primary PCR was 10 cycles and the second 25 cycles.

Measurement of Sequence Abundances Using Internal Standards

As mentioned above various internal standards may be added to amplification reactions of the method in order to estimate absolute quantities of analytes of interest in a sample. For embodiments employing PCR, guidance for designing and preparing internal standards may be found in Roche Molecular Biochemicals Application Note LC 11/2000, or like references. Briefly, a design goal for internal standards is providing a compound with the same amplification efficiency as the target molecule being quantified. Such a goal may be met by selecting an internal standard that includes the following properties: (a) homologous to target molecule (including having the same length and GC content): (b) same primer binding sites as the target molecule; (c) from a well-defined source (e.g. linearized plasmid DNA, purified PCR product, synthetic DNA, or the like); (d) readily detectable (e.g. a distinct sequence easily discernible even in presence of sequencing errors); (e) introduced into reaction in highly accurate concentrations.

Internal standards used with the invention include, but are not limited to, (a) internal standards for quantifying total nucleic acid in a sample (or more precisely, total nucleic acid, or total number of genome equivalents, in the starting material of an amplification reaction): internal standards for total recombined nucleic acids in a sample; and (c) internal standards for total non-recombined nucleic acids in a sample. In one embodiment, internal standards are designed with primers having the same melting and annealing temperatures as those used to amplify clonotypes. In another embodiment, such primers are designed for a two-staged amplification such that primers for second-stage amplification of the internal standards are identical to those used to amplify clonotypes. For example, with reference to FIGS. 2A and 2B, for a first amplification stage, primers of internal standards for the embodiment illustrated may be the same as primer (202) and one (or several) of primers (212), and for a second amplification stage, primers of internal standards may be the same as primer (222) and primer (220).

Generating Sequence Reads for Clonotypes

Any high-throughput technique for sequencing nucleic acids can be used in the method of the invention. Preferably, such technique has a capability of generating in a cost-effective manner a volume of sequence data from which at least 1000 clonotypes can be determined, and preferably, from which at least 10,000 to 1,000,000 clonotypes can be determined. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of the separated molecules has more recently been demonstrated by sequential or single extension reactions using polymerases or ligases as well as by single or sequential differential hybridizations with libraries of probes. These reactions have been performed on many clonal sequences in parallel including demonstrations in current commercial applications of over 100 million sequences in parallel. These sequencing approaches can thus be used to study the repertoire of T-cell receptor (TCR) and/or B-cell receptor (BCR). In one aspect of the invention, high-throughput methods of sequencing are employed that comprise a step of spatially isolating individual molecules on a solid surface where they are sequenced in parallel. Such solid surfaces may include nonporous surfaces (such as in Solexa sequencing, e.g. Bentley et al, Nature, 456: 53-59 (2008) or Complete Genomics sequencing. e.g. Drmanac et al, Science, 327: 78-81 (2010)), arrays of wells, which may include bead- or particle-bound templates (such as with 454, e.g. Margulies et al, Nature, 437: 376-380 (2005) or Ion Torrent sequencing, U.S. patent publication 2010/0137143 or 2010/0304982), micromachined membranes (such as with SMRT sequencing. e.g. Eid et al. Science, 323: 133-138 (2009)), or bead arrays (as with SOLID sequencing or polony sequencing. e.g. Kim et al. Science, 316: 1481-1414 (2007)). In another aspect, such methods comprise amplifying the isolated molecules either before or after they are spatially isolated on a solid surface. Prior amplification may comprise emulsion-based amplification, such as emulsion PCR, or rolling circle amplification. Of particular interest is Solexa-based sequencing where individual template molecules are spatially isolated on a solid surface, after which they are amplified in parallel by bridge PCR to form separate clonal populations, or clusters, and then sequenced, as described in Bentley et al (cited above) and in manufacturer's instructions (e.g. TruSeq™ Sample Preparation Kit and Data Sheet, Illumina, Inc., San Diego, Calif., 2010); and further in the following references: U.S. Pat. Nos. 6,090,592; 6,300,070; 7,115,400; and EP0972081 B1; which are incorporated by reference. In one embodiment, individual molecules disposed and amplified on a solid surface form clusters in a density of at least $10^5$ clusters per $cm^2$; or in a density of at least $5 \times 10^5$ per $cm^2$; or in a density of at least $10^6$ clusters per $cm^2$. In one embodiment, sequencing chemistries are employed having relatively high error rates. In such embodiments, the average quality scores produced by such chemistries are monotonically declining functions of sequence read lengths. In one embodiment, such decline corresponds to 0.5 percent of sequence reads have at least one error in positions 1-75; 1 percent of sequence reads have at least one error in positions 76-100; and 2 percent of sequence reads have at least one error in positions 101-125.

In one aspect, a sequence-based clonotype profile of an individual is obtained using the following steps: (a) obtaining a nucleic acid sample from T-cells and/or B-cells of the individual; (b) spatially isolating individual molecules derived from such nucleic acid sample, the individual molecules comprising at least one template generated from a nucleic acid in the sample, which template comprises a somatically rearranged region or a portion thereof, each individual molecule being capable of producing at least one sequence read; (c) sequencing said spatially isolated individual molecules; and (d) determining abundances of different sequences of the nucleic acid molecules from the nucleic acid sample to generate the clonotype profile. In one embodiment, each of the somatically rearranged regions comprise a V region and a J region. In another embodiment, the step of sequencing comprises bidirectionally sequencing each of the spatially isolated individual molecules to produce at least one forward sequence read and at least one reverse sequence read. Further to the latter embodiment, at least one of the forward sequence reads and at least one of the reverse sequence reads have an overlap region such that bases of such overlap region are determined by a reverse complementary relationship between such sequence reads. In still another embodiment, each of the somatically rearranged regions comprise a V region and a J region and the step of sequencing further includes determining a sequence of each of the individual nucleic acid molecules from one or more of its forward sequence reads and at least one reverse sequence read starting from a position in a J region and extending in the direction of its associated V region. In another embodiment, individual molecules comprise nucleic acids selected from the group consisting of complete IgH molecules, incomplete IgH molecules, complete IgK complete, IgK inactive molecules, TCRβ molecules, TCRγ molecules, complete TCRδ molecules, and incomplete TCRδ molecules. In another embodiment, the step of sequencing comprises generating the sequence reads having monotonically decreasing quality scores. Further to the latter embodiment, monotonically decreasing quality scores are such that the sequence reads have error rates no better than the following: 0.2 percent of sequence reads contain at least one error in base positions 1 to 50, 0.2 to 1.0 percent of sequence reads contain at least one error in positions 51-75, 0.5 to 1.5 percent of sequence reads contain at least one error in positions 76-100. In another embodiment, the above method comprises the following steps: (a) obtaining a nucleic acid sample from T-cells and/or B-cells of the individual; (b) spatially isolating individual molecules derived from such nucleic acid sample, the individual molecules comprising nested sets of templates each generated from a nucleic acid in the sample and each containing a somatically rearranged region or a portion thereof, each nested set being capable of producing a plurality of sequence reads each extending in the same direction and each starting from a different position on the nucleic acid from which the nested set was generated: (c) sequencing said spatially isolated individual molecules; and (d) determining abundances of different sequences of the nucleic acid molecules from the nucleic acid sample to generate the clonotype profile. In one embodiment, the step of sequencing includes producing a plurality of sequence reads for each of the nested sets. In another embodiment, each of the somatically rearranged regions comprise a V region and a J region, and each of the plurality of sequence reads starts from a different position in the V region and extends in the direction of its associated J region.

In one aspect, for each sample from an individual, the sequencing technique used in the methods of the invention generates sequences of least 1000 clonotypes per run; in another aspect, such technique generates sequences of at least 10,000 clonotypes per run: in another aspect, such technique generates sequences of at least 100,000 clonotypes per run; in another aspect, such technique generates sequences of at least 500,000 clonotypes per run; and in another aspect, such technique generates sequences of at least 1,000,000 clonotypes per run. In still another aspect, such technique generates sequences of between 100,000 to 1,000,000 clonotypes per run per individual sample.

The sequencing technique used in the methods of the provided invention can generate about 30 bp, about 40 bp, about 50 bp, about 60 bp, about 70 bp, about 80 bp, about 90 bp, about 100 bp, about 110, about 120 bp per read, about 150 bp, about 200 bp, about 250 bp, about 300 bp, about 350 bp, about 400 bp, about 450 bp, about 500 bp, about 550 bp, or about 600 bp per read.

Clonotype Determination from Sequence Data Without Sequence Tags

Constructing clonotypes from sequence read data depends in part on the sequencing method used to generate such data, as the different methods have different expected read lengths and data quality. In one approach, a Solexa sequencer is employed to generate sequence read data for analysis as described in Faham and Willis, cited above). In one embodiment, a sample is obtained that provides at least $0.5$-$1.0 \times 10^6$ lymphocytes to produce at least 1 million template molecules, which after optional amplification may produce a corresponding one million or more clonal populations of template molecules (or clusters). For most high throughput sequencing approaches, including the Solexa approach, such over sampling at the cluster level is desirable so that each template sequence is determined with a large degree of redundancy to increase the accuracy of sequence determination. For Solexa-based implementations, preferably the sequence of each independent template is determined 10 times or more. For other sequencing approaches with different expected read lengths and data quality, different levels of redundancy may be used for comparable accuracy of sequence determination. Those of ordinary skill in the art recognize that the above parameters, e.g. sample size, redundancy, and the like, are design choices related to particular applications.

Figure 4A:
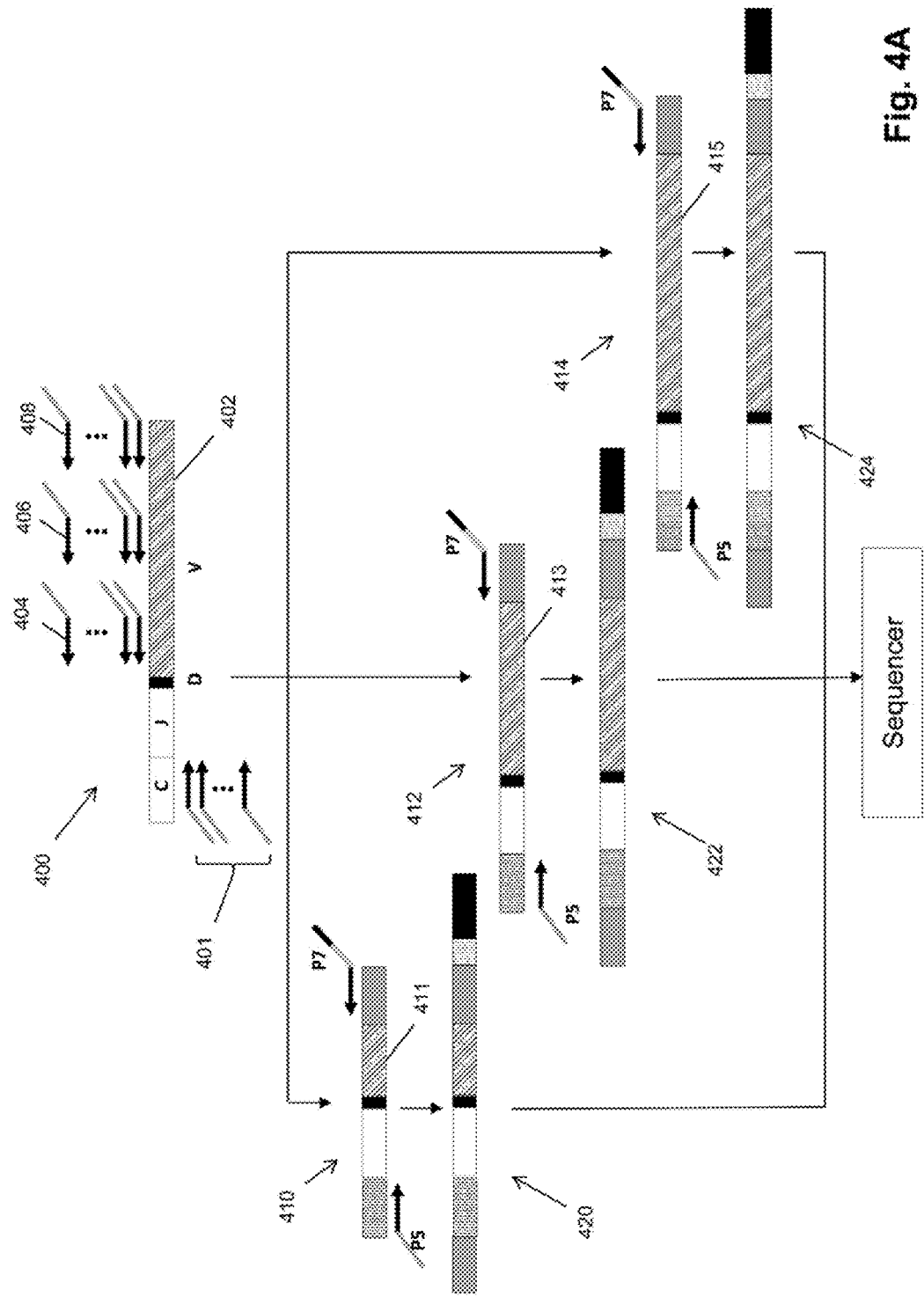
FIG. 4A illustrates a PCR scheme for generating three sequencing templates from an IgH chain in a single reaction.
Figure 4B:
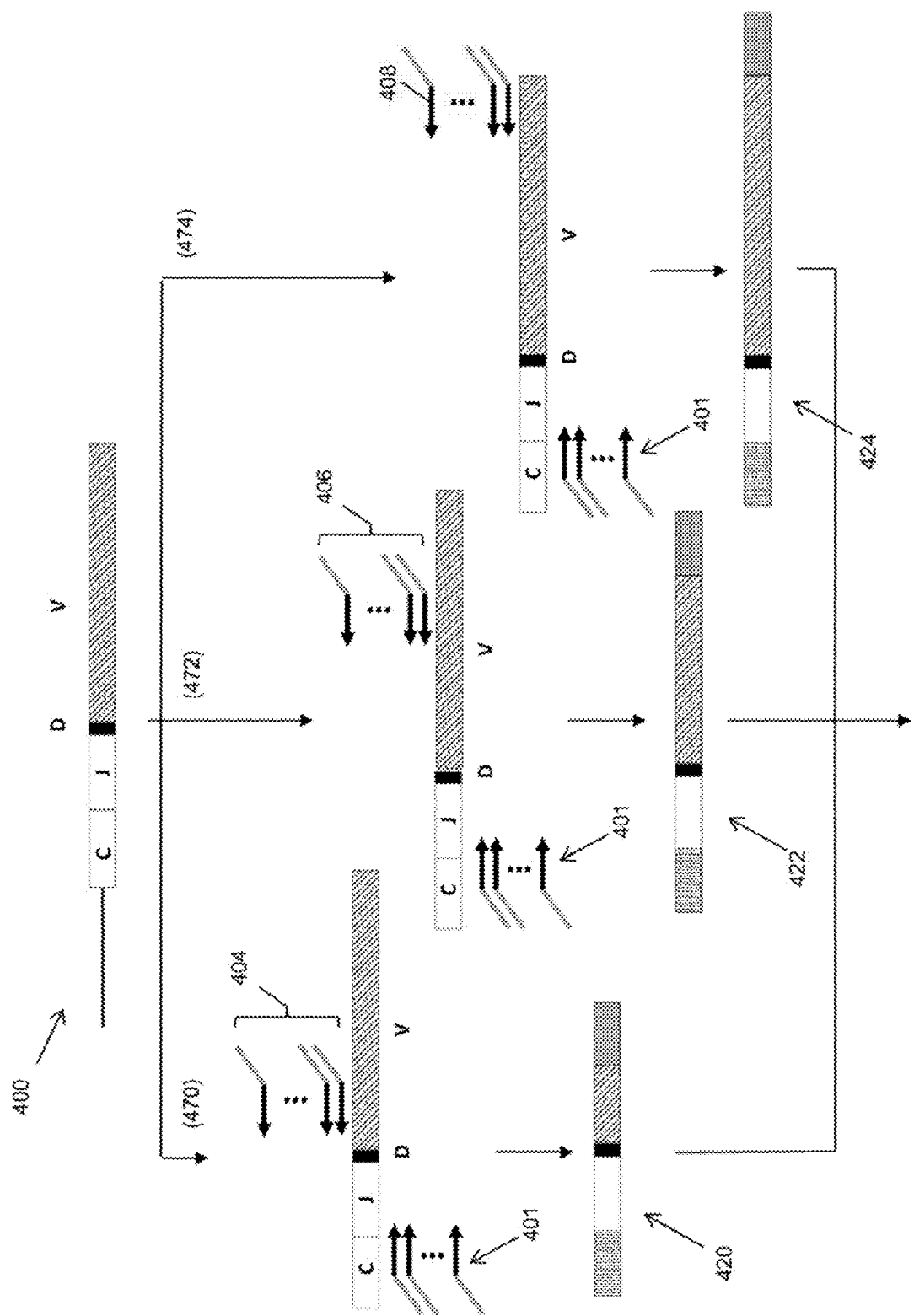
FIGS. 4B-4C illustrates a PCR scheme for generating three sequencing templates from an IgH chain in three separate reactions after which the resulting amplicons are combined for a secondary PCR to add P5 and P7 primer binding sites.
Figure 4C:
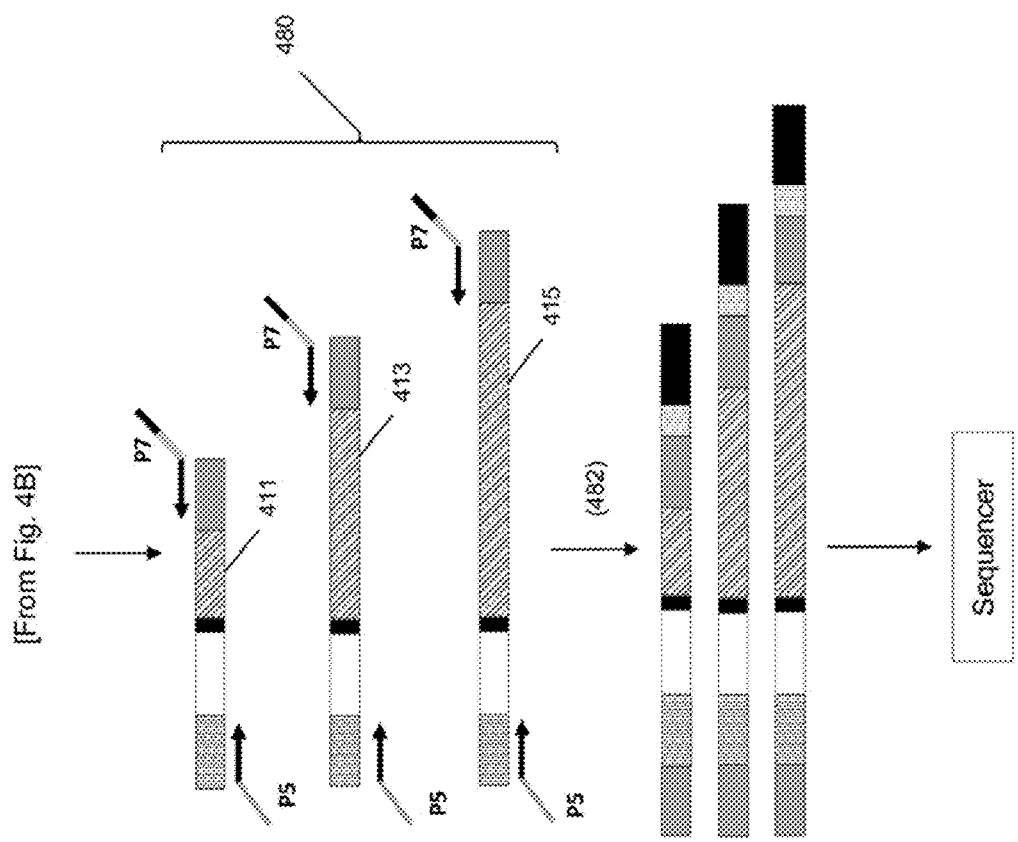

In one aspect of the invention, sequences of clonotypes (including but not limited to those derived from IgH, TCRα, TCRβ, TCRγ, TCRδ, and/or IgLx (IgK)) may be determined by combining information from one or more sequence reads, for example, along the V(D)J regions of the selected chains. In another aspect, sequences of clonotypes are determined by combining information from a plurality of sequence reads. Such pluralities of sequence reads may include one or more sequence reads along a sense strand (i.e. "forward" sequence reads) and one or more sequence reads along its complementary strand (i.e. "reverse" sequence reads). When multiple sequence reads are generated along the same strand, separate templates are first generated by amplifying sample molecules with primers selected for the different positions of the sequence reads. This concept is illustrated in FIG. 4A where primers (404, 406 and 408) are employed to generate amplicons (410, 412, and 414, respectively) in a single reaction. Such amplifications may be carried out in the same reaction or in separate reactions. In one aspect, whenever PCR is employed, separate amplification reactions are used for generating the separate templates which, in turn, are combined and used to generate multiple sequence reads along the same strand. This latter approach is preferable for avoiding the need to balance primer concentrations (and/or other reaction parameters) to ensure equal amplification of the multiple templates (sometimes referred to herein as "balanced amplification" or "unbias amplification"). The generation of templates in separate reactions is illustrated in FIGS. 4B-4C. There a sample containing IgH (400) is divided into three portions (470, 472, and 474) which are added to separate PCRs using J region primers (401) and V region primers (404, 406, and 408, respectively) to produce amplicons (420, 422 and 424, respectively). The latter amplicons are then combined (478) in secondary PCR (480) using P5 and P7 printers to prepare the templates (482) for bridge PCR and sequencing on an Illumina GA sequencer, or like instrument.

Sequence reads of the invention may have a wide variety of lengths, depending in par on the sequencing technique being employed. For example, for some techniques, several tradeoffs may arise in its implementation, for example, (i) the number and lengths of sequence reads per template and (ii) the cost and duration of a sequencing operation. In one embodiment, sequence reads are in the range of from 20 to 400 nucleotides; in another embodiment, sequence reads are in a range of from 30 to 200 nucleotides: in still another embodiment, sequence reads are in the range of from 30 to 120 nucleotides. In one embodiment, 1 to 4 sequence reads are generated for determining the sequence of each clonotype; in another embodiment, 2 to 4 sequence reads are generated for determining the sequence of each clonotype; and in another embodiment, 2 to 3 sequence reads are generated for determining the sequence of each clonotype. In the foregoing embodiments, the numbers given are exclusive of sequence reads used to identify samples from different individuals. The lengths of the various sequence reads used in the embodiments described below may also vary based on the information that is sought to be captured by the read; for example, the starting location and length of a sequence read may be designed to provide the length of an NDN region as well as its nucleotide sequence; thus, sequence reads spanning the entire NDN region are selected. In other aspects, one or more sequence reads that in combination (but not separately) encompass a D and/or NDN region are sufficient.

In another aspect of the invention, sequences of clonotypes are determined in part by aligning sequence reads to one or more V region reference sequences and one or more J region reference sequences, and in part by base determination without alignment to reference sequences, such as in the highly variable NDN region. A variety of alignment algorithms may be applied to the sequence reads and reference sequences. For example, guidance for selecting alignment methods is available in Batzoglou. Briefings in Bioinformatics, 6: 6-22 (2005), which is incorporated by reference. In one aspect, whenever V reads or C reads (as mentioned above) are aligned to V and J region reference sequences, a tree search algorithm is employed, e.g. as described generally in Gusfield (cited above) and Cormen et al, Introduction to Algorithms. Third Edition (The MIT Press, 2009).

Figure 3A:
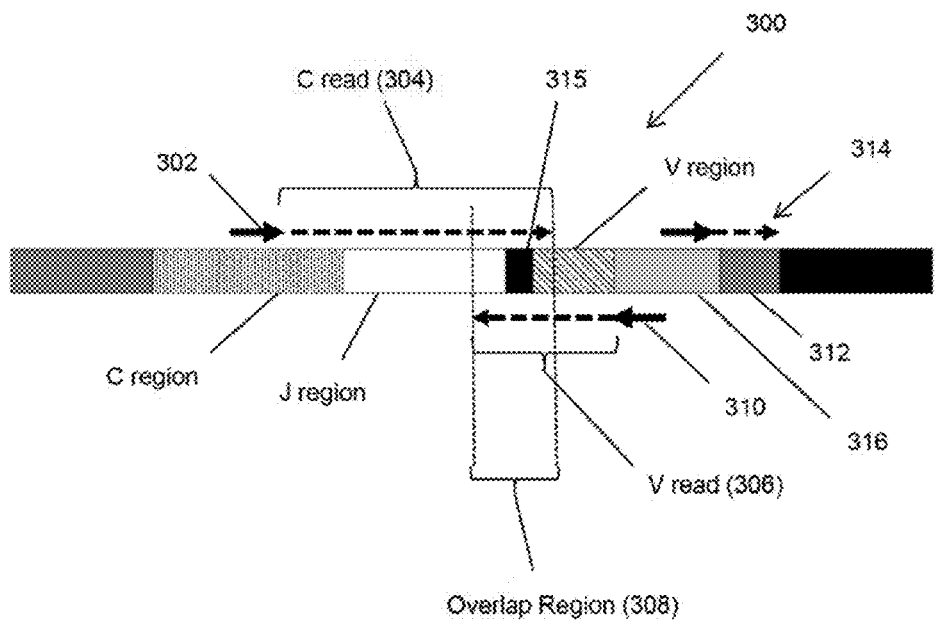
FIG. 3A illustrates details of determining a nucleotide sequence of the PCR product of FIG. 2C.
Figure 3B:
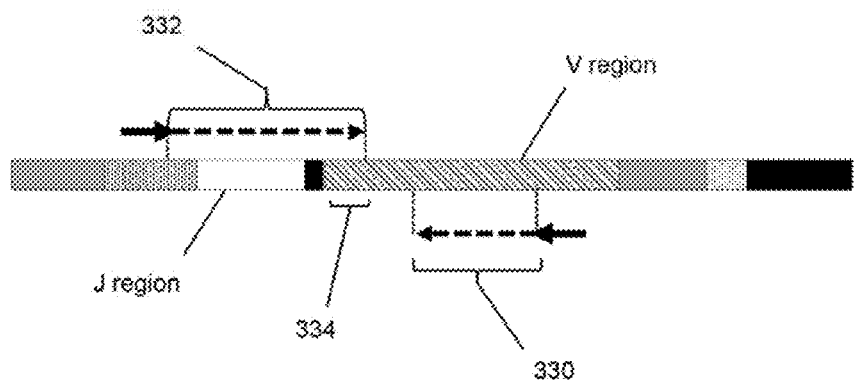
FIG. 3B illustrates details of another embodiment of determining a nucleotide sequence of the PCR product of FIG. 2C.

In another aspect, an end of at least one forward read and an end of at least one reverse read overlap in an overlap region (e.g. 308 in FIG. 3A), so that the bases of the reads are in a reverse complementary relationship with one another. Thus, for example, if a forward read in the overlap region is "5'-acgttgc", then a reverse read in a reverse complementary relationship is "5'-gcaacgt" within the same overlap region. In one aspect, bases within such an overlap region are determined, at least in part, from such a reverse complementary relationship. That is, a likelihood of a base call (or a related quality score) in a prospective overlap region is increased if it preserves, or is consistent with, a reverse complementary relationship between the two sequence reads. In one aspect, clonotypes of TCR II and IgH chains (illustrated in FIG. 3A) are determined by at least one sequence read starting in its J region and extending in the direction of its associated V region (referred to herein as a "C read" (304)) and at least one sequence read starting in its V region and extending in the direction of its associated J region (referred to herein as a "V read" (306)). Overlap region (308) may or may not encompass the NDN region (315) as shown in FIG. 3A. Overlap region (308) may be entirely in the J region, entirely in the NDN region, entirely in the V region, or it may encompass a J region-NDN region boundary or a V region-NDN region boundary, or both such boundaries (as illustrated in FIG. 3A). Typically, such sequence reads are generated by extending sequencing primers, e.g. (302) and (310) m FIG. 3A, with a polymerase in a sequencing-by-synthesis reaction, e.g. Metzger, Nature Reviews Genetics, 11: 31-46 (2010); Fuller et al, Nature Biotechnology, 27: 1013-1023 (2009). The binding sites for primers (302) and (310) are predetermined, so that they can provide a starting point or anchoring point for initial alignment and analysis of the sequence reads. In one embodiment, a C read is positioned so that it encompasses the D and/or NDN region of the TCR β or IgH chain and includes a portion of the adjacent V region, e.g. as illustrated in FIGS. 3A and 3B. In one aspect, the overlap of the V read and the C read in the V region is used to align the reads with one another. In other embodiments, such alignment of sequence reads is not necessary, e.g. with TCRβ chains, so that a V read may only be long enough to identify the particular V region of a clonotype. This latter aspect is illustrated in FIG. 3B. Sequence read (330) is used to identify a V region, with or without overlapping another sequence read, and another sequence read (332) traverses the NDN region and is used to determine the sequence thereof. Portion (334) of sequence read (332) that extends into the V region is used to associate the sequence information of sequence read (332) with that of sequence read (330) to determine a clonotype. For some sequencing methods, such as base-by-base approaches like the Solexa sequencing method, sequencing run time and reagent costs are reduced by minimizing the number of sequencing cycles in an analysis. Optionally, as illustrated in FIG. 3A, amplicon (300) is produced with sample tag (312) to distinguish between clonotypes originating from different biological samples. e.g. different patients. Sample tag (312) may be identified by annealing a primer to primer binding region (316) and extending it (314) to produce a sequence read across tag (312), from which sample tag (312) is decoded.

The IgH chain is more challenging to analyze than TCRβ chain because of at least two factors: i) the presence of somatic mutations makes the mapping or alignment more difficult, and ii) the NDN region is larger so that it is often not possible to map a portion of the V segment to the C read. In one aspect of the invention, this problem is overcome by using a plurality of primer sets for generating V reads, which are located at different locations along the V region, preferably so that the primer binding sites are nonoverlapping and spaced apart, and with at least one primer binding site adjacent to the NDN region, e.g. in one embodiment from 5 to 50 bases from the V-NDN junction, or in another embodiment from 10 to 50 bases from the V-NDN junction. The redundancy of a plurality of primer sets minimizes the risk of failing to detect a clonotype due to a failure of one or two primers having binding sites affected by somatic mutations. In addition, the presence of at least one primer binding site adjacent to the NDN region makes it more likely that a V read will overlap with the C read and hence effectively extend the length of the C read. This allows for the generation of a continuous sequence that spans all sizes of NDN regions and that can also map substantially the entire V and J regions on both sides of the NDN region. Embodiments for carrying out such a scheme are illustrated in FIGS. 4A and 4D. In FIG. 4A, a sample comprising IgH chains (400) are sequenced by generating a plurality amplicons for each chain by amplifying the chains with a single set of J region primers (401) and a plurality (three shown) of sets of V region (402) primers (404, 406, 408) to produce a plurality of nested amplicons (e.g. 410, 412, 416) all comprising the same NDN region and having different lengths encompassing successively larger portions (411, 413, 415) of V region (402). Members of a nested set may be grouped together after sequencing by noting the identify (or substantial identity) of their respective NDN, J and/or C regions, thereby allowing reconstruction of a longer V(D)J segment than would be the case otherwise for a sequencing platform with limited read length and/or sequence quality. In one embodiment, the plurality of primer sets may be a number in the range of from 2 to 5. In another embodiment the plurality is 2-3; and still another embodiment the plurality is 3. The concentrations and positions of the primers in a plurality may vary widely. Concentrations of the V region primers may or may not be the same. In one embodiment, the primer closest to the NDN region has a higher concentration than the other primers of the plurality, e.g. to insure that amplicons containing the NDN region are represented in the resulting amplicon. In a particular embodiment where a plurality of three primers is employed, a concentration ratio of 60:20:20 is used. One or more primers (e.g. 435 and 437 in FIG. 4D) adjacent to the NDN region (444) may be used to generate one or more sequence reads (e.g. 434 and 436) that overlap the sequence read (442) generated by J region primer (432), thereby improving the quality of base calls in overlap region (440). Sequence reads from the plurality of primers may or may not overlap the adjacent downstream primer binding site and/or adjacent downstream sequence read. In one embodiment, sequence reads proximal to the NDN region (e.g. 436 and 438) may be used to identify the particular V region associated with the clonotype. Such a plurality of primers reduces the likelihood of incomplete or failed amplification in case one of the primer binding sites is hypermutated during immunoglobulin development. It also increases the likelihood that diversity introduced by hypermutation of the V region will be capture in a clonotype sequence. A secondary PCR may be performed to prepare the nested amplicons for sequencing, e.g. by amplifying with the P5 (401) and P7 (404. 406, 408) primers as illustrated to produce amplicons (420, 422, and 424), which may be distributed as single molecules on a solid surface, where they are further amplified by bridge PCR, or like technique.

Base calling in NDN regions (particularly of IgH chains) can be improved by using the codon structure of the flanking J and V regions, as illustrated in FIG. 4E. (As used herein, "codon structure" means the codons of the natural reading frame of segments of TCR or BCR transcripts or genes outside of the NDN regions. e.g. the V region, J region, or the like.) There amplicon (450), which is an enlarged view of the amplicon of FIG. 4B, is shown along with the relative positions of C read (442) and adjacent V read (434) above and the codon structures (452 and 454) of V region (430) and J region (446), respectively, below. In accordance with this aspect of the invention, after the codon structures (452 and 454) are identified by conventional alignment to the V and J reference sequences, bases in NDN region (456) are called (or identified) one base at a time moving from J region (446) toward V region (430) and in the opposite direction from V region (430) toward J region (446) using sequence reads (434) and (442). Under normal biological conditions, only the recombined TCR or IgH sequences that have in frame codons from the V region through the NDN region and to the J region are expressed as proteins. That is, of the variants generated somatically only ones expressed are those whose J region and V region codon frames are in-frame with one another and remain in-frame through the NDN region. (Here the correct frames of the V and J regions are determined from reference sequences). If an out-of-frame sequence is identified based one or more low quality base calls, the corresponding clonotype is flagged for re-evaluation or as a potential disease-related anomaly. If the sequence identified is in-frame and based on high quality base calls, then there is greater confidence that the corresponding clonotype has been correctly called. Accordingly, in one aspect, the invention includes a method of determining V(D)J-based clonotypes from bidirectional sequence reads comprising the steps of: (a) generating at least one J region sequence read that begins in a J region and extends into an NDN region and at least one V region sequence read that begins in the V regions and extends toward the NDN region such that the J region sequence read and the V region sequence read are overlapping in an overlap region, and the J region and the V region each have a codon structure: (b) determining whether the codon structure of the J region extended into the NDN region is in frame with the codon structure of the V region extended toward the NDN region. In a further embodiment, the step of generating includes generating at least one V region sequence read that begins in the V region and extends through the NDN region to the J region, such that the J region sequence read and the V region sequence read are overlapping in an overlap region.

Somatic Hypermutations. In one embodiment, IgH-based clonotypes that have undergone somatic hypermutation are determined as follows. A somatic mutation is defined as a sequenced base that is different from the corresponding base of a reference sequence (of the relevant segment, usually V, J or C) and that is present in a statistically significant number of reads. In one embodiment, C reads may be used to find somatic mutations with respect to the mapped J segment and likewise V reads for the V segment. Only pieces of the C and V reads are used that are either directly mapped to J or V segments or that are inside the clonotype extension up to the NDN boundary. In this way, the NDN region is avoided and the same 'sequence information' is not used for mutation finding that was previously used for clonotype determination (to avoid erroneously classifying as mutations nucleotides that are really just different recombined NDN regions). For each segment type, the mapped segment (major allele) is used as a scaffold and all reads are considered which have mapped to this allele during the read mapping phase. Each position of the reference sequences where at least one read has mapped is analyzed for somatic mutations. In one embodiment, the criteria for accepting a non-reference base as a valid mutation include the following: 1) at least N reads with the given mutation base, 2) at least a given fraction N/M reads (where M is the total number of mapped reads at this base position) and 3) a statistical cut based on the binomial distribution, the average Q score of the N reads at the mutation base as well as the number (M-N) of reads with a non-mutation base. Preferably, the above parameters are selected so that the false discovery rate of mutations per clonotype is less than 1 in 1000, and more preferably, less than 1 in 10000.

Kits of the Invention

The invention includes kits comprising materials and reagents for carrying out the methods of the invention. In one embodiment, kits of the invention comprise primers and recombined sequence internal standards for determining total amount or concentration of recombined nucleic acids in a tissue sample. In another embodiment, kits of the invention include (a) primers and recombined sequence internal standards for determining total amount or concentration of recombined nucleic acids in a tissue sample and (b) primers and total nucleic acid internal standards for determining total amount or concentration of total nucleic acids in a tissue sample. In one aspect of the latter embodiment, such total nucleic acid internal standard is selected or derived from the group consisting of constitutively and universally expressed housekeeping genes: in a further such aspect, such total nucleic acid internal standard is selected or derived from the group consisting of the following genes: GAPDH, $\beta_2$-microglobulin, 18S ribosomal RNA, and $\beta$-actin. In another embodiment, kits of the invention include (a) primers and recombined sequence internal standards for determining total amount or concentration of recombined nucleic acids in a tissue sample, (b) primers and total nucleic acid internal standards for determining total amount or concentration of total nucleic acids in a tissue sample, and (c) primers and first and/or second excised segment internal standards for determining total amount or concentration of nonrecombined nucleic acids in a tissue sample. In still another embodiment, kits of the invention include (a) primers and recombined sequence internal standards for determining total amount or concentration of recombined nucleic acids in a tissue sample, (b) primers and total nucleic acid internal standards for determining total amount or concentration of total nucleic acids in a tissue sample, (c) primers and first and/or second excised segment internal standards for determining total amount or concentration of nonrecombined nucleic acids in a tissue sample, and (d) primers for determining the value of alleles of genetic markers at one or more genetic loci located in both recombined nucleic acids and nonrecombined nucleic acids. In still another embodiment, kits of the invention include (a) primers and recombined sequence internal standards for determining total amount or concentration of recombined nucleic acids in a tissue sample, (b) primers and total nucleic acid internal standards for determining total amount or concentration of total nucleic acids in a tissue sample, (c) primers for determining the value of alleles of genetic markers at one or more genetic loci present in nonrecombined nucleic acids and absent in recombined nucleic acids, and (d) primers for determining the value of alleles of genetic markers at one or more genetic loci located in both recombined nucleic acids and nonrecombined nucleic acids.

In further regard of all of the above embodiments, primers of a kit for amplifying a genetic marker may include for one or more of the genetic marker at least one forward primer specific to an upstream flanking region and at least one reverse primer specific to a downstream flanking region. Likewise, in further regard of all of the above embodiments, primers of a kit may comprise a set of pairs of forward primer and reverse primer, wherein each forward primer has a tail and each reverse primer has a tail. As used herein, "tail" means a portion of a primer that serves as a primer binding site in a second stage of a two-stage amplification reaction. Preferably, a tail is not complementary to sequences in the nucleic acids being amplified, in particular, to those at or near a flanking region. In a further embodiment, the primer binding site of all the tails of forward primers of the pairs have the same sequence and the primer binding site of all the tails of reverse primers of the pairs have the same sequence. In still a further embodiment, the sequences of the primer binding sites of the tails of the pairs of forward and reverse primers are different.

While the present invention has been described with reference to several particular example embodiments, those skilled in the art will recognize that many changes may be made thereto without departing from the spirit and scope of the present invention. The present invention is applicable to a variety of implementations and other subject matter, in addition to those discussed above.

DEFINITIONS

Unless otherwise specifically defined herein, terms and symbols of nucleic acid chemistry, biochemistry, genetics, and molecular biology used herein follow those of standard treatises and texts in the field, e.g. Komberg and Baker, DNA Replication, Second Edition (W.H. Freeman. New York, 1992); Lehninger, Biochemistry. Second Edition (Worth Publishers. New York, 1975) Strachan and Read. Human Molecular Genetics. Second Edition (Wiley-Liss. New York, 1999); Abbas et al, Cellular and Molecular Immunology, 6$^{th}$ edition (Saunders, 2007).

"Aligning" means a method of comparing a test sequence, such as a sequence read, to one or more reference sequences to determine which reference sequence or which portion of a reference sequence is closest based on some sequence distance measure. An exemplary method of aligning nucleotide sequences is the Smith Waterman algorithm. Distance measures may include Hamming distance, Levenshtein distance, or the like. Distance measures may include a component related to the quality values of nucleotides of the sequences being compared.

"Amplicon" means the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide legations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4.683.202; 4,800,159 (PCR); Gelfand et al, U.S. Pat. No. 5,210,015 (real-time PCR with "taqman" probes); Wittwer et al, U.S. Pat. No. 6,174,670; Kacian et al. U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but be not limited to, buffering agents to maintain pH at a selected level during a reaction, salts, co-factors, scavengers, and the like.

"Clonality" as used herein means a measure of the degree to which the distribution of clonotype abundances among clonotypes of a repertoire is skewed to a single or a few clonotypes. Roughly, clonality is an inverse measure of clonotype diversity. Many measures or statistics are available from ecology describing species-abundance relationships that may be used for clonality measures in accordance with the invention, e.g. Chapters 17 & 18, in Pielou, An Introduction to Mathematical Ecology, (Wiley-Interscience, 1969). In one aspect, a clonality measure used with the invention is a function of a clonotype profile (that is, the number of distinct clonotypes detected and their abundances), so that after a clonotype profile is measured, clonality may be computed from it to give a single number. One clonality measure is Simpson's measure, which is simply the probability that two randomly drawn clonotypes will be the same. Other clonality measures include information-based measures and McIntosh's diversity index, disclosed in Pielou (cited above).

"Clonotype" means a recombined nucleotide sequence of a lymphocyte which encodes an immune receptor or a portion thereof. More particularly, clonotype means a recombined nucleotide sequence of a T cell or B cell which encodes a T cell receptor (TCR) or B cell receptor (BCR), or a portion thereof. In various embodiments, clonotypes may encode all or a portion of a VDJ rearrangement of IgH, a DJ rearrangement of IgH, a VJ rearrangement of IgK, a VJ rearrangement of IgL, a VDJ rearrangement of TCR β, a DJ rearrangement of TCR β, a VJ rearrangement of TCR α, a VJ rearrangement of TCR γ, a VDJ rearrangement of TCR δ, a VD rearrangement of TCR δ, a Kde-V rearrangement, or the like. Clonotypes may also encode translocation breakpoint regions involving immune receptor genes, such as BcII-IgH or Bcll-IgH. In one aspect, clonotypes have sequences that are sufficiently long to represent or reflect the diversity of the immune molecules that they are derived from; consequently, clonotypes may vary widely in length. In some embodiments, clonotypes have lengths in the range of from 25 to 400 nucleotides; in other embodiments, clonotypes have lengths in the range of from 25 to 200 nucleotides.

"Clonotype profile" means a listing of distinct clonotypes and their relative abundances that are derived from a population of lymphocytes. Typically, the population of lymphocytes are obtained from a tissue sample. The term "clonotype profile" is related to, but more general than, the immunology concept of immune "repertoire" as described in references, such as the following: Arstila et al. Science, 286: 958-61 (1999): Yassai et al. Imnunogenetics, 61: 493-502 (2009); Kedzierska et al, Mol. Immunol., 45(3): 607-618 (2008); and the like. The term "clonotype profile" includes a wide variety of lists and abundances of rearranged immune receptor-encoding nucleic acids, which may be derived from selected subsets of lymphocytes (e.g. tissue-infiltrating lymphocytes, immunophenotypic subsets, or the like), or which may encode portions of immune receptors that have reduced diversity as compared to full immune receptors. In some embodiments, clonotype profiles may comprise at least $10^3$ distinct clonotypes; in other embodiments, clonotype profiles may comprise at least $10^4$ distinct clonotypes; in other embodiments, clonotype profiles may comprise at least $10^5$ distinct clonotypes; in other embodiments, clonotype profiles may comprise at least $10^6$ distinct clonotypes. In such embodiments, such clonotype profiles may further comprise abundances or relative frequencies of each of the distinct clonotypes. In one aspect, a clonotype profile is a set of distinct recombined nucleotide sequences (with their abundances) that encode T cell receptors (TCRs) or B cell receptors (BCRs), or fragments thereof, respectively, in a population of lymphocytes of an individual, wherein the nucleotide sequences of the set have a one-to-one correspondence with distinct lymphocytes or their clonal subpopulations for substantially all of the lymphocytes of the population. In one aspect, nucleic acid segments defining clonotypes are selected so that their diversity (i.e. the number of distinct nucleic acid sequences in the set) is large enough so that substantially every T cell or B cell or clone thereof in an individual carries a unique nucleic acid sequence of such repertoire. That is, preferably each different clone of a sample has different clonotype. In other aspects of the invention, the population of lymphocytes corresponding to a repertoire may be circulating B cells, or may be circulating T cells, or may be subpopulations of either of the foregoing populations, including but not limited to, CD4+ T cells, or CD8+ T cells, or other subpopulations defined by cell surface markers, or the like. Such subpopulations may be acquired by taking samples from particular tissues, e.g. bone marrow, or lymph nodes, or the like, or by sorting or enriching cells from a sample (such as peripheral blood) based on one or more cell surface markers, size, morphology, or the like. In still other aspects, the population of lymphocytes corresponding to a repertoire may be derived from disease tissues, such as a tumor tissue, an infected tissue, or the like. In one embodiment, a clonotype profile comprising human TCR β chains or fragments thereof comprises a number of distinct nucleotide sequences in the range of from $0.1 \times 10^6$ to $1.8 \times 10^6$, or in the range of from $0.5 \times 10^6$ to $1.5 \times 10^5$, or in the range of from $0.8 \times 10^6$ to $1.2 \times 10^6$. In another embodiment, a clonotype profile comprising human IgH chains or fragments thereof comprises a number of distinct nucleotide sequences in the range of from $0.1 \times 10^6$ to $1.8 \times 10^6$, or in the range of from $0.5 \times 10^6$ to $1.5 \times 10^6$, or in the range of from $0.8 \times 10^6$ to $1.2 \times 10^6$. In a particular embodiment, a clonotype profile of the invention comprises a set of nucleotide sequences encoding substantially all segments of the V(D)J region of an IgH chain. In one aspect, "substantially all" as used herein means every segment having a relative abundance of 0.001 percent or higher; or in another aspect, "substantially all" as used herein means every segment having a relative abundance of 0.0001 percent or higher. In another particular embodiment, a clonotype profile of the invention comprises a set of nucleotide sequences that encodes substantially all segments of the V(D)J region of a TCR t chain. In another embodiment, a clonotype profile of the invention comprises a set of nucleotide sequences having lengths in the range of from 25-200 nucleotides and including segments of the V, D, and J regions of a TCR β chain. In another embodiment, a clonotype profile of the invention comprises a set of nucleotide sequences having lengths in the range of from 25-200 nucleotides and including segments of the V, D, and J regions of an IgH chain. In another embodiment, a clonotype profile of the invention comprises a number of distinct nucleotide sequences that is substantially equivalent to the number of lymphocytes expressing a distinct IgH chain. In another embodiment, a clonotype profile of the invention comprises a number of distinct nucleotide sequences that is substantially equivalent to the number of lymphocytes expressing a distinct TCR β chain. In still another embodiment, "substantially equivalent" means that with ninety-nine percent probability a clonotype profile will include a nucleotide sequence encoding an IgH or TCR β or portion thereof carried or expressed by every lymphocyte of a population of an individual at a frequency of 0.001 percent or greater. In still another embodiment. "substantially equivalent" means that with ninety-nine percent probability a repertoire of nucleotide sequences will include a nucleotide sequence encoding an IgH or TCR β or portion thereof carried or expressed by every lymphocyte present at a frequency of 0.0001 percent or greater. In some embodiments, clonotype profiles are derived from samples comprising from $10^5$ to $10^7$ lymphocytes. Such numbers of lymphocytes may be obtained from peripheral blood samples of from 1-10 mL.

"Coalescing" means treating two candidate clonotypes with sequence differences as the same by determining that such differences are due to experimental or measurement error and not due to genuine biological differences. In one aspect, a sequence of a higher frequency candidate clonotype is compared to that of a lower frequency candidate clonotype and if predetermined criteria are satisfied then the number of lower frequency candidate clonotypes is added to that of the higher frequency candidate clonotype and the lower frequency candidate clonotype is thereafter disregarded. That is, the read counts associated with the lower frequency candidate clonotype are added to those of the higher frequency candidate clonotype.

"Complementarity determining regions" (CDRs) mean regions of an immunoglobulin (i.e., antibody) or T cell receptor where the molecule complements an antigen's conformation, thereby determining the molecule's specificity and contact with a specific antigen. T cell receptors and immunoglobulins each have three CDRs: CDR1 and CDR2 are found in the variable (V) domain, and CDR3 includes some of V, all of diverse (D) (heavy chains only) and joint (J), and some of the constant (C) domains.

"Contamination" as used herein means the presence in a tissue sample of one individual of nucleic acid from another individual. In one aspect, "contamination" means the presence of nucleic acid not originating from a patient which may affect the interpretation of a clonotype profile of the patient.

"Genetic identification" means a unique correspondence between an individual and a set of values (or states) of genetic markers from one or more genetic loci of the individual.

"Genetic marker" means a polymorphic segment of DNA at a genetic locus, which may be used to identify an individual. A genetic marker many be identified by its sequence or by adjacent or flanking sequences. Typically, a genetic marker can have a plurality of sequences, or values, in different individuals of a population. Exemplary genetic markers include, but are not limited to, short tandem repeats (STRs), single nucleotide polymorphisms (SNPs), and the like. The polymorphic segment of DNA may be genomic DNA or it may be reverse transcribed RNA. In one embodiment, the polymorphic segment is genomic DNA. In one embodiment, a genetic marker for use with the invention is identified by amplification and sequencing using conventional techniques. In another embodiment, genetic markers are amplified and sequenced together with immune molecules during the process for generating a clonotype profile.

"Internal standard" means a nucleic acid sequence that is processed in the same reaction as one or more target polynucleotides in order to permit absolute or relative quantification of the target polynucleotides in a sample. In one aspect the reaction is an amplification reaction, such as PCR. An internal standard may be endogenous or exogenous. That is, an internal standard may occur naturally in the sample, or it may be added to the sample prior to a reaction. In one aspect, one or more exogenous internal standard sequences may be added to a reaction mixture in predetermined concentrations to provide a calibration to which an amplified sequence may be compared to determine the quantity of its corresponding target polynucleotide in a sample. Selection of the number, sequences, lengths, and other characteristics of exogenous internal standards is a routine design choice for one of ordinary skill in the art. Endogenous internal standards, also referred to herein as "reference sequences," are sequences natural to a sample that correspond to minimally regulated genes that exhibit a constant and cell cycle-independent level of transcription, e.g. Selvey et al. Mol. Cell Probes, 15: 307-3111 (2001). Exemplary internal standards include, but are not limited to, sequences from the following genes: GAPDH. $\beta_2$-microglobulin, 18S ribosomal RNA, and $\beta$-actin.

"Kit" refers to any delivery system for delivering materials or reagents for carrying out a method of the invention. In the context of methods of the invention, such delivery systems include systems that allow for the storage, transport, or delivery of reaction reagents (e.g., primers, enzymes, internal standards, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains primers.

"Lymphoid neoplasm" means an abnormal proliferation of lymphocytes that may be malignant or non-malignant. A lymphoid cancer is a malignant lymphoid neoplasm. Lymphoid neoplasms are the result of, or are associated with, lymphoproliferative disorders, including but not limited to follicular lymphoma, chronic lymphocytic leukemia (CLL), acute lymphocytic leukemia (ALL), hairy cell leukemia, lymphomas, multiple myeloma, post-transplant lymphoproliferative disorder, mantle cell lymphoma (MCL), diffuse large B cell lymphoma (DLBCL). T cell lymphoma, or the like, e.g. Jaffe et al, Blood, 112: 4384-4399 (2008): Swerdlow et al, WHO Classification of Tumours of Haematopoietic and Lymphoid Tissues (e. $4^{th}$) (IARC Press, 2008).

"Minimal residual disease" means remaining cancer cells after treatment. The term is most frequently used in connection with treatment of lymphomas and leukemias.

"Pecent homologous," "percent identical" or like terms used in reference to the comparison of a reference sequence and another sequence ("comparison sequence") mean that in an optimal alignment between the two sequences, the comparison sequence is identical to the reference sequence in a number of subunit positions equivalent to the indicated percentage, the subunits being nucleotides for polynucleotide comparisons or amino acids for polypeptide comparisons. As used herein, an "optimal alignment" of sequences being compared is one that maximizes matches between subunits and minimizes the number of gaps employed in constructing an alignment. Percent identities may be determined with commercially available implementations of algorithms, such as that described by Needleman and Wunsch. J. Mol. Biol., 48: 443-453 (1970)("GAP" program of Wisconsin Sequence Analysis Package, Genetics Computer Group. Madison, Wis.), or the like. Other software packages in the art for constructing alignments and calculating percentage identity or other measures of similarity include the "BestFit" program, based on the algorithm of Smith and Waterman, Advances in Applied Mathematics, 2: 482-489 (1981) (Wisconsin Sequence Analysis Package. Genetics Computer Group, Madison, Wis.). In other words, for example, to obtain a polynucleotide having a nucleotide sequence at least 95 percent identical to a reference nucleotide sequence, up to five percent of the nucleotides in the reference sequence may be deleted or substituted with another nucleotide, or a number of nucleotides up to five percent of the total number of nucleotides in the reference sequence may be inserted into the reference sequence.

"Polymerase chain reaction." or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al. editors. PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. The particular format of PCR being employed is discernible by one skilled in the art from the context of an application. Reaction volumes range from a few hundred nanoliters, e.g. 200 nL, to a few hundred μL, e.g. 20 μL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670) and 6.569.627 (intercalating dyes): Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999) two-color real-time PCR). Usually, distinct sets of primers are employed for each sequence being amplified. Typically, the number of target sequences in a multiplex PCR is in the range of from 2 to 50, or from 2 to 40, or from 2 to 30. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences or internal standards that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin. GAPDH, β$_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996): Diviacco et al, Gene, 122: 3013-3020 (1992): Becker-Andre et al, Nucleic Acids Research, 17: 9437-9446 (1989); and the like.

"Polynucleotide" refers to a linear polymer of nucleotide monomers and may be DNA or RNA. Monomers making up polynucleotides are capable of specifically binding to a natural polynucleotide by way of a regular pattern of monomer-to-monomer interactions, such as Watson-Crick type of base pairing, base stacking. Hoogsteen or reverse Hoogsteen types of base pairing, or the like. Such monomers and their internucleosidic linkages may be naturally occurring or may be analogs thereof, e.g., naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Polynucleotides may comprise the four natural nucleosides (e.g. deoxyadenosine, deoxycytidine, deoxyguanosine, deoxythymidine for DNA or their ribose counterparts for RNA) linked by phosphodiester linkages. However, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity (e.g. single stranded DNA, RNA/DNA duplex, or the like), then selection of an appropriate composition for the oligonucleotide or polynucleotide substrates is well within the knowledge of one of ordinary skill, especially with guidance from treatises such as Sambrook et al, MOLECULAR CLONING, 2nd ed. (Cold Spring Harbor Laboratory. New York, 1989), and like references. As used herein, the term "oligonucleotide" refers to smaller polynuckotides, for example, having 3-60 monomeric units, or in some embodiments having from 12 to 60 monomeric units. In various embodiments, a polynucleotide or oligonucleotides may be represented by a sequence of letters (upper or lower case), such as "ATGCCTG," and it will be understood that the nucleotides are in 5'→3' order from left to right and that "A" denotes deoxyadenosine, "C" denotes deoxycytidine. "G" denotes deoxyguanosine, and "T" denotes thymidine. "I" denotes deoxyinosine, "U" denotes uridine, unless otherwise indicated or obvious from context.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, 2$^{nd}$ Edition (Cold Spring Harbor Press, New York, 2003).

"Quality score" means a measure of the probability that a base assignment at a particular sequence location is correct. A variety methods are well known to those of ordinary skill for calculating quality scores for particular circumstances, such as, for bases called as a result of different sequencing chemistries, detection systems, base-calling algorithms, and so on. Generally, quality score values are monotonically related to probabilities of correct base calling. For example, a quality score, or Q, of 10 may mean that there is a 90 percent chance that a base is called correctly, a Q of 20 may mean that there is a 99 percent chance that a base is called correctly, and so on. For some sequencing platforms, particularly those using sequencing-by-synthesis chemistries, average quality scores decrease as a function of sequence read length, so that quality scores at the beginning of a sequence read are higher than those at the end of a sequence read, such declines being due to phenomena such as incomplete extensions, carry forward extensions, loss of template, loss of polymerase, capping failures, deprotection failures, and the like.

"Sequence read" means a sequence of nucleotides determined from a sequence or stream of data generated by a sequencing technique, which determination is made, for example, by means of base-calling software associated with the technique, e.g. base-calling software from a commercial provider of a DNA sequencing platform. A sequence read usually includes quality scores for each nucleotide in the sequence. Typically, sequence reads are made by extending a primer along a template nucleic acid, e.g. with a DNA polymerase or a DNA ligase. Data is generated by recording signals, such as optical, chemical (e.g. pH change), or electrical signals, associated with such extension. Such initial data is converted into a sequence read.

"Sequence tag" (or "tag") or "barcode" means an oligonucleotide that is attached to a polynucleotide or template molecule and is used to identify and/or track the polynucleotide or template in a reaction or a series of reactions. A sequence tag may be attached to the 3'- or 5'-end of a polynucleotide or template or it may be inserted into the interior of such polynucleotide or template to form a linear conjugate, sometime referred to herein as a "tagged polynucleotide." or "tagged template." or "tag-polynucleotide conjugate," "tag-molecule conjugate," or the like. Sequence tags may vary widely in size and compositions: the following references, which are incorporated herein by reference, provide guidance for selecting sets of sequence tags appropriate for particular embodiments; Brenner. U.S. Pat. No. 5,635,400; Brenner and Macevicz, U.S. Pat. No. 7,537,897; Brenner et al, Proc. Natl. Acad. Sci., 97: 1665-1670 (2000); Church et al, European patent publication 0 303 459; Shoemaker et al, Nature Genetics, 14: 450-456 (1996); Morris et al. European patent publication 0799897 A1; Wallace. U.S. Pat. No. 5,981,179: and the like. Lengths and compositions of sequence tags can vary widely, and the selection of particular lengths and/or compositions depends on several factors including, without limitation, how tags are used to generate a readout. e.g. via a hybridization reaction or via an enzymatic reaction, such as sequencing; whether they are labeled, e.g. with a fluorescent dye or the like; the number of distinguishable oligonucleotide tags required to unambiguously identify a set of polynucleotides, and the like, and how different must tags of a set be in order to ensure reliable identification, e.g. freedom from cross hybridization or misidentification from sequencing errors. In one aspect, sequence tags can each have a length within a range of from 2 to 36 nucleotides, or from 4 to 30 nucleotides, or from 8 to 20 nucleotides, or from 6 to 10 nucleotides, respectively. In one aspect, sets of sequence tags are used wherein each sequence tag of a set has a unique nucleotide sequence that differs from that of every other tag of the same set by at least two bases; in another aspect, sets of sequence tags are used wherein the sequence of each tag of a set differs from that of every other tag of the same set by at least three bases.

"Sequence tree" means a tree data structure for representing nucleotide sequences. In one aspect, a tree data structure of the invention is a rooted directed tree comprising nodes and edges that do not include cycles, or cyclical pathways. Edges from nodes of tree data structures of the invention are usually ordered. Nodes and/or edges are structures that may contain, or be associated with, a value. Each node in a tree has zero or more child nodes, which by convention are shown below it in the tree. A node that has a child is called the child's parent node. A node has at most one parent. Nodes that do not have any children are called leaf nodes. The topmost node in a tree is called the root node. Being the topmost node, the root node will not have parents. It is the node at which operations on the tree commonly begin (although some algorithms begin with the leaf nodes and work up ending at the root). All other nodes can be reached from it by following edges or links.

"Short tandem repeats" or "STRs" or "microsatellites" refer to genetic markers comprising a short (e.g., 1-5 nucleotide), tandemly repeated sequence motif. Microsatellites may contain repeat-motif interspersions, or "cryptically simple sequence" (Tauts, D. et al. (1986) *Nature* 322(6080): 652-656), Such repeat-motif interspersions include simple repeat-motif interspersions wherein the microsatellite contains one or more interspersed repeats with the same length as the tandemly repeated sequence motif, but a different repeat sequence (Eichler, E.E. et al. (1994) *Nat. Genet.* 8:88-94; Eichler, E. E. et al. (1996) *Hum. Mol. Genet.* 5:319-330). For example, if the tandemly repeated sequence motif is TGCC, a simple repeat-motif interspersion may appear as follows: $TGCC(TCTG)_2(TGCC)_3$ (SEQ ID NO: 5), wherein the interspersed repeat "TCTG" interrupts the repeat of the TGCC tandem repeated sequence motif. Repeat-motif interspersions also include more complex repeat-motif interspersions wherein the repeat motif interspersion is not the same length as the tandem repeated sequence motif. Other more complex repeat motif interspersions include the combination of the simple repeat-motif interspersion and the complex repeat-motif interspersion in the same microsatellite. Microsatellites and without interspersed repeats are encompassed by the terms "microsatellites"or "STR" as used herein.

What is claimed is:

1. A method of determining carry over contamination in a sample containing T cells and/or B cells in vitro, comprising:
 determining a clonotype profile for each of a plurality of samples by the following steps:
  (i) attaching sequence tags to molecules of recombined nucleic acids of T-cell receptor genes or immunoglobulin genes of the T-cells and/or B-cells to form tag-molecule conjugates, wherein substantially every molecule of the tag-molecule conjugates has a unique sequence tag;
  (ii) amplifying the tag-molecule conjugates;
  (iii) sequencing the tag-molecule conjugates to produce sequence reads that each comprise a sequence tag portion and a clonotype portion; and
  (iv) aligning like sequence tag portions of the sequence reads to determine a clonotype sequence from corresponding clonotype portions of the aligned sequence reads and generating a clonotype profile from the clonotype portions; and
 recording nucleotide sequences of the sequence tags of each measurement of a clonotype profile; and
 determining carry over contamination in the sample by the presence, absence and/or level of sequence tags from any clonotype profile of said plurality of samples.

2. The method of claim 1, wherein said step of aligning further includes determining the nucleotide sequence of each of said clonotype of each of said tag-molecule conjugate by determining a majority nucleotide at each nucleotide position of said clonotypes of said like sequence tag portions.

3. The method of claim 1, wherein said step of attaching includes labeling by sampling said molecules of recombined nucleic acids.

4. The method of claim 3, wherein said step of attaching is implemented in a reaction mixture such that said sequence tags are present in the reaction mixture in a concentration at least 100 times that of said molecules of recombined nucleic acids.

5. The method of claim 4, wherein said sequence tags are incorporated into primers specific for said molecules of recombined nucleic acids.

6. The method of claim 1, wherein said clonotypes are each 25 to 400 nucleotides in length encoding a segment of an immune receptor or immune receptor component selected from the group consisting of a VDJ rearrangement of IgH, a DJ rearrangement of IgH, a VJ rearrangement of IgK, a VJ rearrangement of IgL, a VDJ rearrangement of TCR β, a DJ rearrangement of TCR β, a VJ rearrangement of TCR α, a VJ rearrangement of TCR γ, a VDJ rearrangement of TCR δ, and a VD rearrangement of TCR δ.

7. The method of claim 1, wherein determining carry over contamination comprises measuring the presence, absence, and/or level of sequence tags from any prior clonotype profile and comparing such against a subsequent clonotype profile.

8. The method of claim 1, wherein the presence of a unique sequence tag shared amongst said any clonotype profile of said plurality of samples indicates a carry over contamination event.

* * * * *

SEQUENCE LISTING

```
<160> NUMBER OF SEQ ID NOS: 5

<210> SEQ ID NO 1
<211> LENGTH: 22
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(22)
<223> OTHER INFORMATION: n is a, c, g, or t

<400> SEQUENCE: 1
nnnnnnnnnn nnnnnnnnnn nn                                               22

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
agttctggct aacctgtaga gcca                                             24

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
agttcgggct aacctgtaga gcca                                             24

<210> SEQ ID NO 4
<211> LENGTH: 24
<212> TYPE: DNA
<213> ORGANISM: Artificial Sequence
<220> FEATURE:
```

```
<223> OTHER INFORMATION: primer

<400> SEQUENCE: 4
agttccggct aacctgtaga tcca                                          24

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
tgcctctgtc tgtgcctgcc tgcc                                          24
```